(12) United States Patent
Friedlander et al.

(10) Patent No.: US 7,788,213 B2
(45) Date of Patent: Aug. 31, 2010

(54) SYSTEM AND METHOD FOR A MULTIPLE DISCIPLINARY NORMALIZATION OF SOURCE FOR METADATA INTEGRATION WITH ETL PROCESSING LAYER OF COMPLEX DATA ACROSS MULTIPLE CLAIM ENGINE SOURCES IN SUPPORT OF THE CREATION OF UNIVERSAL/ENTERPRISE HEALTHCARE CLAIMS RECORD

(75) Inventors: Robert R. Friedlander, Southbury, CT (US); Richard A. Hennessy, Austin, TX (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 417 days.

(21) Appl. No.: 11/760,652

(22) Filed: Jun. 8, 2007

(65) Prior Publication Data

US 2008/0307430 A1    Dec. 11, 2008

(51) Int. Cl.
*G06F 17/00* (2006.01)
(52) U.S. Cl. .................. 707/600; 707/601; 707/602; 707/756; 707/809
(58) Field of Classification Search ................ 707/101, 707/102, 600, 601, 602, 809
See application file for complete search history.

(56) References Cited

U.S. PATENT DOCUMENTS

| | | | |
|---|---|---|---|
| 5,890,115 A * | 3/1999 | Cole | 704/258 |
| 6,611,838 B1 | 8/2003 | Ignat et al. | |
| 6,615,258 B1 | 9/2003 | Barry et al. | |
| 2004/0083199 A1 * | 4/2004 | Govindugari et al. | 707/1 |
| 2004/0255281 A1 * | 12/2004 | Imamura et al. | 717/141 |
| 2005/0235274 A1 | 10/2005 | Mamou et al. | |
| 2006/0052945 A1 * | 3/2006 | Rabinowitz et al. | 702/20 |
| 2006/0136194 A1 * | 6/2006 | Armstrong et al. | 704/4 |
| 2007/0130206 A1 | 6/2007 | Zhou et al. | |
| 2007/0185869 A1 | 8/2007 | Kimak | |
| 2007/0245013 A1 * | 10/2007 | Saraswathy et al. | 709/223 |
| 2007/0274154 A1 * | 11/2007 | Simon et al. | 367/38 |
| 2009/0254572 A1 | 10/2009 | Redlich et al. | |

* cited by examiner

*Primary Examiner*—Mohammad Ali
*Assistant Examiner*—Thuy (Tiffany) Bui
(74) *Attorney, Agent, or Firm*—Yee & Associates, P.C.; John R. Pivnichny

(57) ABSTRACT

Exemplary illustrative embodiments provide for a computer implemented method, apparatus, and computer usable program code for mapping data. The mapping is defined by a user and maps a source datum to a target datum having a target attribute. The mapping is defined using metadata. Source specific information is omitted from the mapping and stored in a target data repository.

17 Claims, 11 Drawing Sheets

900

| | SOURCE ATTRIBUTE | TARGET DOMAIN | |
|---|---|---|---|
| 906 | DOB | AGE | 924 |
| 908 | M OR F | GENDER | 930 |
| 910 | ETHNICITY | ETHNIC ORIGIN | 932 |
| 912 | BMI | BMI METRIC | 926 |
| 912 | BMI | BMI IN TEXT | 928 |
| 914 | HT | HEIGHT IN METRIC | 934 |
| 916 | AGE IN MONTHS | AGE | 924 |
| 918 | SOURCE ATTRIBUTE | DRUG NAME | 936 |
| 920 | SOURCE ATTRIBUTE | DRUG CLASS | 938 |
| 922 | SOURCE ATTRIBUTE | DOSAGE | 940 |

902 — SOURCE ATTRIBUTE; 904 — TARGET DOMAIN
942 — DEMOGRAPHICS; 944 — DRUGS

| SOURCE DATA | CONFORMED DATA TARGET | SEMANTIC MAPPING RULE | |
|---|---|---|---|
| 0 | MALE | NUMBER GENDER CONVERSION | 1010 |
| 1 | FEMALE | NUMBER GENDER CONVERSION | |
| -- | UNKNOWN | NUMBER GENDER CONVERSION | |
| 480 | 40 | MONTHS AGE CONVERSION | 1014 |
| 1/1/70 | 37 | DOB AGE CONVERSION | 1016 |

1002 — SOURCE DATA; 1004 — CONFORMED DATA TARGET; 1006 — SEMANTIC MAPPING RULE
1008 — DEMOGRAPHICS; GENDER
1012 — DEMOGRAPHICS; AGE

*FIG. 10*

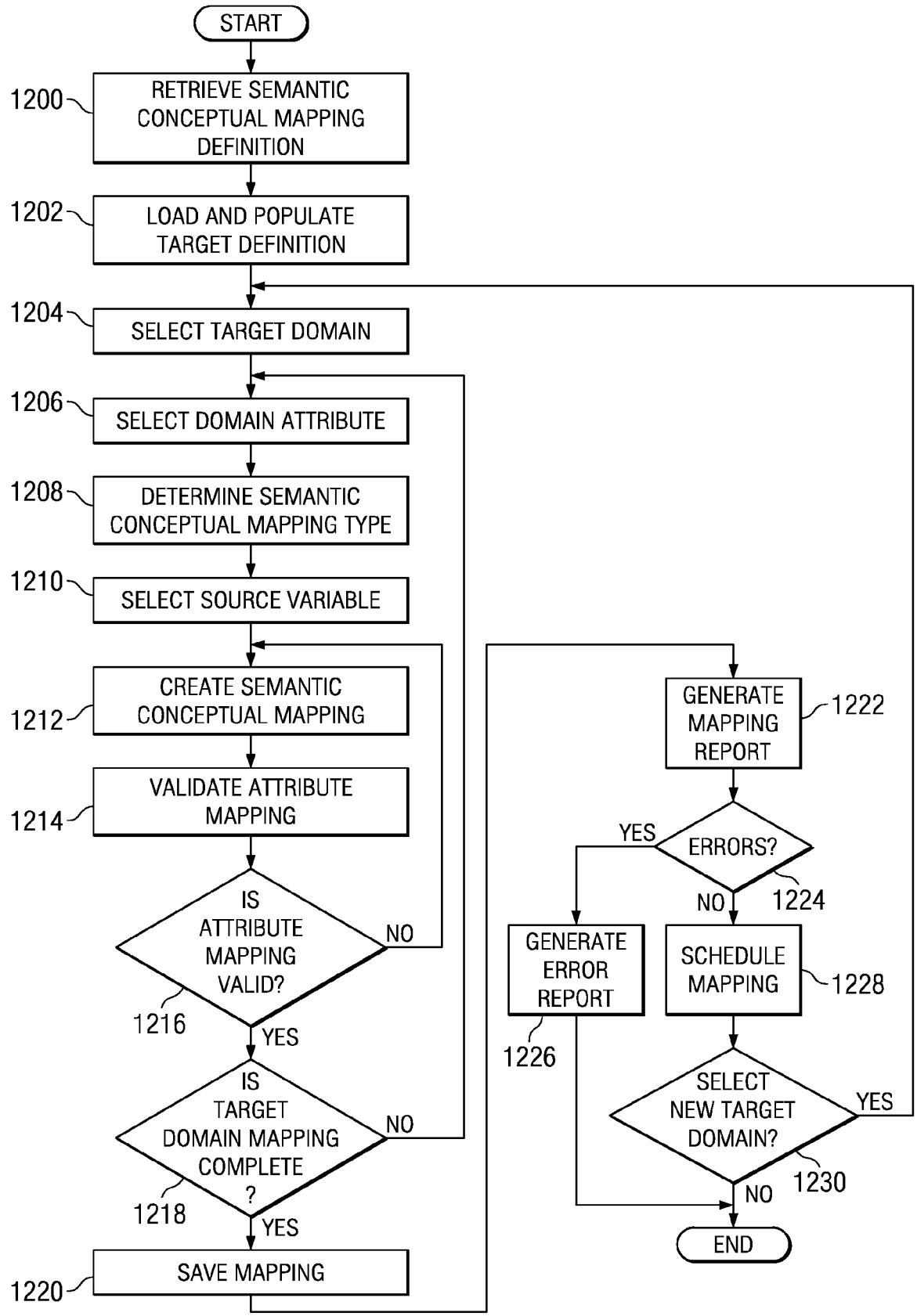

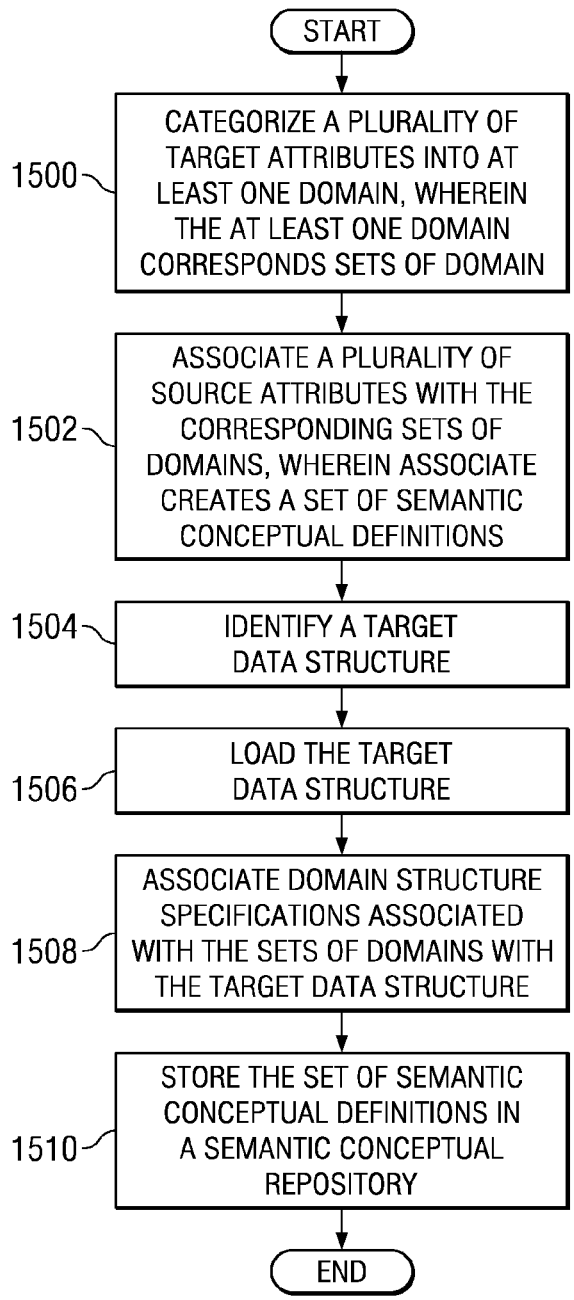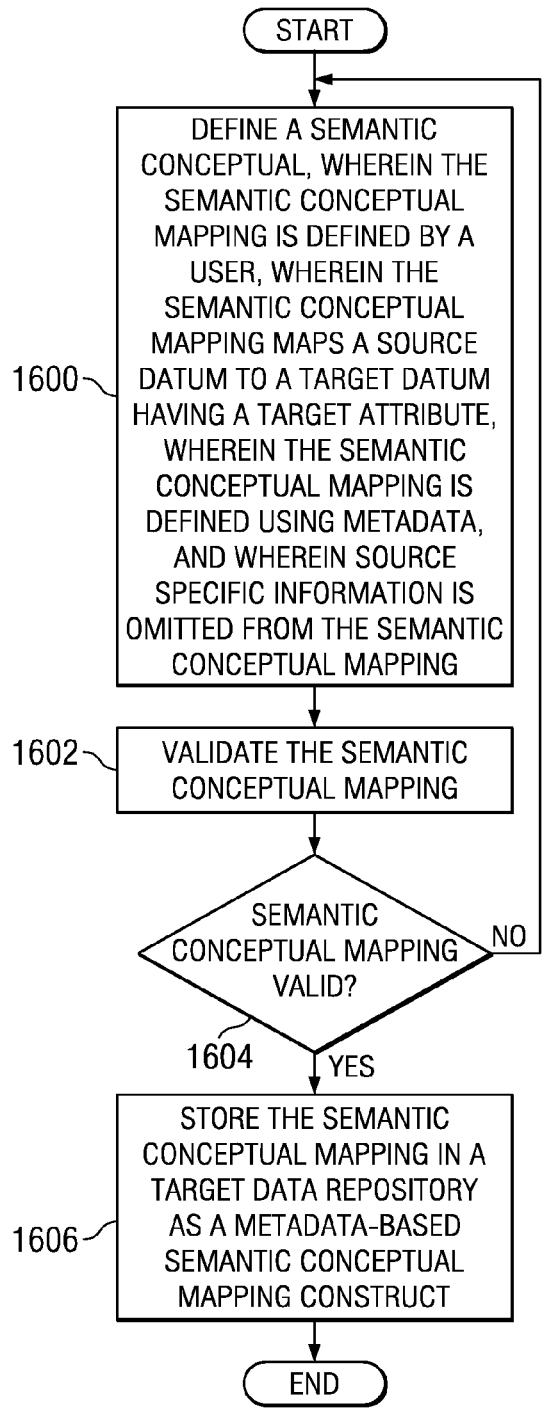

SYSTEM AND METHOD FOR A MULTIPLE DISCIPLINARY NORMALIZATION OF SOURCE FOR METADATA INTEGRATION WITH ETL PROCESSING LAYER OF COMPLEX DATA ACROSS MULTIPLE CLAIM ENGINE SOURCES IN SUPPORT OF THE CREATION OF UNIVERSAL/ENTERPRISE HEALTHCARE CLAIMS RECORD

BACKGROUND OF THE INVENTION

1. Field of the Invention

The present invention relates generally to an improved data processing system and in particular to a method and apparatus for mapping semantically different data from one or more sources to a conformed data set in a target enterprise. Still more particularly, the present invention relates to a computer implemented method, apparatus, and a computer usable program product for defining semantic level concept mapping definitions to enable the utilization of standard extract, transform, and loading process from data source to data target using metadata semantic concept mapping, particularly in a clinical research environment.

2. Description of the Related Art

A continuing problem in information management is the desire to transfer information stored in one format into information stored in another format. Transfer of information may be desired in order to take advantage of new software, to incorporate older information created in individual past projects into newer forms, to compile information in a central repository, or for other reasons. Particularly in the area of clinical research, clinical researchers often encounter the problem of analyzing healthcare or life sciences data, where such data is located in a wide variety of disparate clinical studies, protocols, file systems and/or repositories located on a variety of disparate computing environments. Additionally, the various forms of data can lack semantic equivalency. Semantic equivalency means that the same terms refer to the same concepts in the same manner. Thus, for example, patient records could refer to "gender" as "M_F," "0_1," "Male/Female," or any number of other terms that have the same meaning but not the same name as the term "gender."

Traditionally, integration of healthcare or life sciences data has been performed by information technology specialists who have the high degree of knowledge required to map the various forms of data into a target data repository, such that the data in the target data repository has a desired format. However, these information technology specialists are usually not subject matter experts with regard to healthcare or life sciences research.

Thus, two significant roadblocks exist with regard to performing new analysis and hypothesis generation support in healthcare and life sciences research. The first roadblock is that few information technology specialists have the expertise required to perform the extract, transform, and loading (ETL) process necessary to transform one form of data into a target data repository. Thus, availability of these experts can hamper or delay the desired transfer of data. The second roadblock is that the information technology specialists may not perform optimal mappings or may not perform mappings of most interest to clinical researchers, because the information technology specialists are not aware of issues that relate to the desired clinical research.

In addition to these two roadblocks, even after information technology specialists have created an extract, transform, and load program or plan, such a program or plan is handcrafted to the precise project at hand. Thus, each individual data transfer project is source specific, possibly target specific, and has little capability for reuse by other research projects. As a result, other research projects are forced to "reinvent the wheel" every time an extract, transform, and load process is to be performed from one or more sources of data to a target data repository.

SUMMARY OF THE INVENTION

Exemplary illustrative embodiments provide for a computer implemented method, apparatus, and computer usable program code for mapping data. A rule set is received. The rule set defines a semantic conceptual mapping between a source attribute of a source datum and a target attribute of a target domain. Furthermore, the rule set is implemented using first metadata associated with the source datum. A semantic conceptual construct is created based on the rule set. The semantic conceptual construct describes the semantic conceptual mapping and defines a semantic normalization rule. The semantic conceptual construct is stored in format that supports interaction with a tool for performing an extract, transform, and load process. The source datum is mapped to the target domain using the tool. The tool performs the semantic conceptual mapping using the semantic conceptual construct. A conformed datum is created by the semantic conceptual mapping. The conformed datum is stored in a target data repository.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

FIG. 9 is a table showing an exemplary semantic conceptual mapping from source attributes to target domains, organized by subtype, in accordance with an illustrative embodiment;

FIG. 10 is a table showing an exemplary semantic conceptual mapping from source data to target data using a semantic mapping rule, in accordance with an illustrative embodiment;

FIG. 12 is a flowchart illustrating a method of mapping source data to a domain attribute using a semantic conceptual mapping, in accordance with an illustrative embodiment;

FIG. 15 is a flowchart illustrating performing an extract, transform, and load process using a metadata-based semantic conceptual mapping, in accordance with an illustrative embodiment; and FIG. 16 is a flowchart illustrating performing an extract, transform, and load process using a metadata-based semantic conceptual mapping, in accordance with an illustrative embodiment.

DETAILED DESCRIPTION OF THE PREFERRED EMBODIMENT

Figure 1:
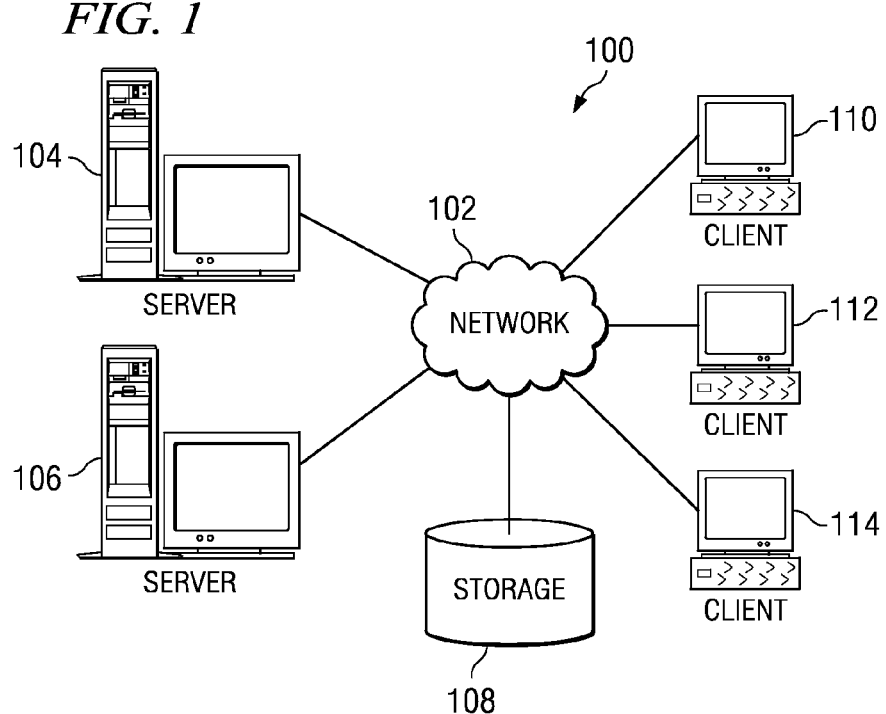
FIG. 1 is a pictorial representation of a network of data processing systems, in which illustrative embodiments may be implemented.
Figure 2:
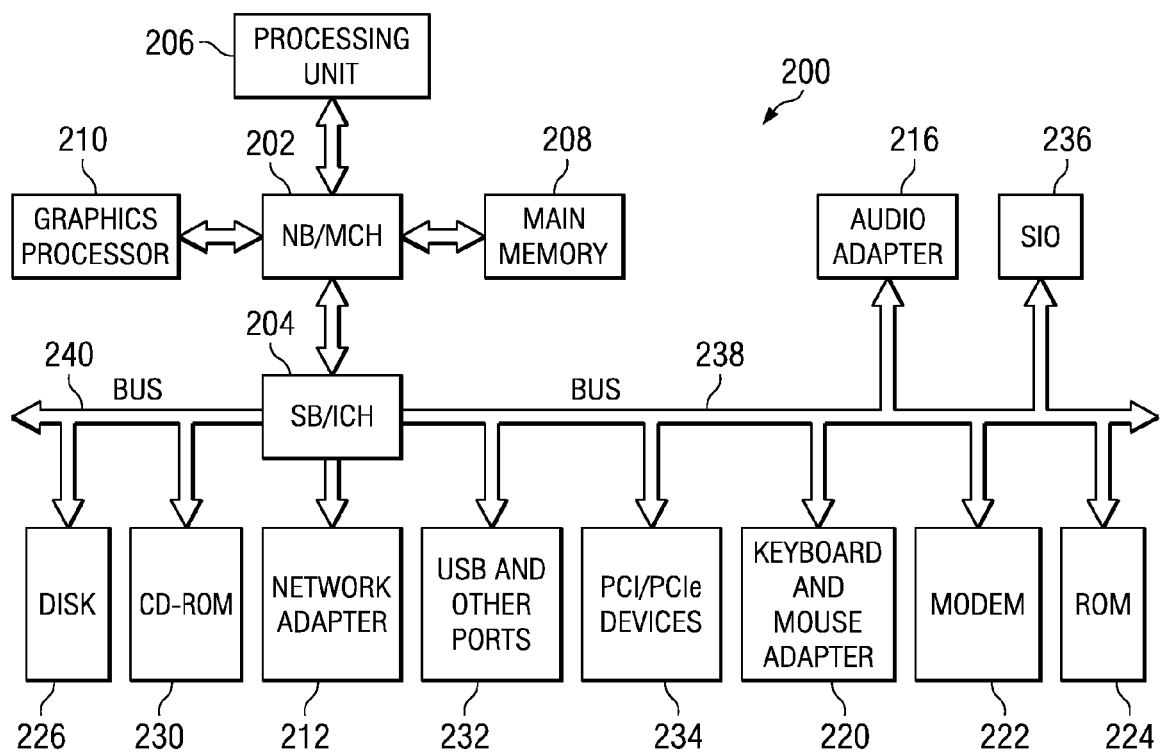
FIG. 2 is a block diagram of a data processing system, in which illustrative embodiments may be implemented.

With reference now to the figures and in particular with reference to FIGS. 1-2, exemplary diagrams of data processing environments are provided, in which illustrative embodiments may be implemented. It should be appreciated that FIGS. 1-2 are only exemplary and are not intended to assert or imply any limitation with regard to the environments, in which different embodiments may be implemented. Many modifications to the depicted environments may be made.

FIG. 1 depicts a pictorial representation of a network of data processing systems, in which illustrative embodiments may be implemented. Network data processing system 100 is a network of computers, in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. Servers 104 and 106 can be file servers used with the illustrative embodiments described herein. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 and 106 in this example. Network data processing system 100 may include additional servers, clients, and other devices not shown.

Network 102 can be used to transmit data between a source of data and a target data repository. Network 102 can also be used to transmit mapping definitions created using the illustrative embodiments to one or more data processing systems for performing an extract, transform, and load process.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

With reference now to FIG. 2, a block diagram of a data processing system is shown in which illustrative embodiments may be implemented. Data processing system 200 is an example of a computer, such as server 104 or client 110 in FIG. 1, in which computer usable program code or instructions implementing the processes may be located for the illustrative embodiments.

In the depicted example, data processing system 200 employs a hub architecture including a north bridge and memory controller hub (NB/MCH) 202 and a south bridge and input/output (I/O) controller hub (SB/ICH) 204. Processing unit 206, main memory 208, and graphics processor 210 are coupled to north bridge and memory controller hub 202. Processing unit 206 may contain one or more processors and even may be implemented using one or more heterogeneous processor systems. Graphics processor 210 may be coupled to the NB/MCH through an accelerated graphics port (AGP), for example.

In the depicted example, local area network (LAN) adapter 212 is coupled to south bridge and I/O controller hub 204 and audio adapter 216, keyboard and mouse adapter 220, modem 222, read only memory (ROM) 224, universal serial bus (USB) and other ports 232, and PCI/PCIe devices 234 are coupled to south bridge and I/O controller hub 204 through bus 238, and hard disk drive (HDD) 226 and CD-ROM 230 are coupled to south bridge and I/O controller hub 204 through bus 240. PCI/PCIe devices may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM 230 may use, for example, an integrated drive electronics (IDE) or serial advanced technology attachment (SATA) interface. A super I/O (SIO) device 236 may be coupled to south bridge and I/O controller hub 204.

An operating system runs on processing unit 206 and coordinates and provides control of various components within data processing system 200 in FIG. 2. The operating system may be a commercially available operating system, such as Microsoft® Windows® XP (Microsoft and Windows are trademarks of Microsoft Corporation in the United States, other countries, or both). An object oriented programming system, such as the JAVA™ programming system, may run in conjunction with the operating system and provides calls to the operating system from JAVA™ programs or applications executing on data processing system 200. JAVA™ and all JAVA™-based trademarks are trademarks of Sun Microsystems, Inc. in the United States, other countries, or both.

Instructions for the operating system, the object-oriented programming system, and applications or programs are located on storage devices, such as hard disk drive 226, and may be loaded into main memory 208 for execution by processing unit 206. The processes of the illustrative embodiments may be performed by processing unit 206 using computer implemented instructions, which may be located in a memory such as, for example, main memory 208, read only memory 224, a storage device, a hard drive, or in one or more peripheral devices.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. Also, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may be comprised of one or more buses, such as a system bus, an I/O bus and a PCI bus. Of course, the bus system may be implemented using any type of communications fabric or architecture that provides for a transfer of data between different components or devices attached to the fabric or architecture. A communications unit may include one or more devices used to transmit and receive data, such as a modem or a network adapter. A memory may be, for example, main memory 208 or a cache, such as found in north bridge and memory controller hub 202. A processing unit may include one or more processors or CPUs. The depicted examples in FIGS. 1-2 and above-described examples are not meant to imply architectural limitations. For example, data processing system 200 also may be a tablet computer, laptop computer, or telephone device in addition to taking the form of a PDA.

Exemplary illustrative embodiments provide for a computer implemented method, apparatus, and computer usable program code for mapping data. A rule set is received. The rule set defines a semantic conceptual mapping between a source attribute of a source datum and a target attribute of a target domain. Furthermore, the rule set is implemented using first metadata associated with the source datum. A semantic conceptual construct is instantiated or created in the semantic conceptual construct based on the rule set. The semantic conceptual construct specifies the semantic normalization that should occur. For example, a semantic conceptual normalization could be changing 0 to Male, 1 to Female, A to Male, B to Female, and others. A semantic conceptual normalization is manifested in a manner to support standardized interactions with a tool that performs an extract, transform, and load process. The ETL process executed by the tool extracts the semantic rules from semantic conceptual construct, and will enforce them upon executing a job involving a source/target combination. Thus, the rules are triggered upon mapping the source datum to the target domain using the tool. The tool performs the mapping leveraging the semantic rules specified or described in the semantic conceptual construct. A conformed datum is created by the semantic conceptual mapping. The conformed datum is stored in a target data repository.

As used herein, the term "semantic conceptual construct" refers to a semantic concept mapping of a first data object to a second data object, wherein metadata specify the structure and semantics of the first data object, such that the first data object can be mapped to the second data object. The semantic conceptual mapping is defined by a user and maps a source datum to a target datum having a target attribute. The semantic conceptual mapping is defined using metadata and results in the generation of metadata which stores the semantic mapping rule set. As used herein, metadata is data that describes another set of data. Metadata can contain data describing a source, a target, and/or semantic conceptual mapping rules.

This exemplary embodiment can be used to create extract, transform, and load processes without reference to the source attributes during a high-level mapping on a graphical user interface. Reference to source attributes is performed automatically by the exemplary embodiments after the user has graphically specified the mapping.

Specifically, the process of defining the mappings can be performed using semantic conceptual mappings, as described herein, without reference to source attributes. The semantic conceptual mapping tool, itself, can create the references from source attributes to target domain attributes via semantic conceptual constructs. Thus, the illustrative embodiments provide for defining a semantic conceptual mapping, wherein the semantic conceptual mapping is defined by a user, wherein the semantic conceptual mapping maps a source datum to a target datum having a target attribute, wherein the semantic conceptual mapping is defined using metadata, and wherein source specific information is omitted from the semantic conceptual mapping. The semantic conceptual mapping can be stored in a target data repository.

As stated before, users who have limited information technology knowledge can use the exemplary embodiments to define semantic conceptual mappings from an unclean source of data to a target data repository. The term "limited information technology knowledge" means that the individual in question lacks the knowledge to create a known extract, transform, and load process, such as that shown in FIG. 3 or FIG. 4. The illustrative embodiments can then, in conjunction with available tools, execute the extract, transform, and load process. These processes are particularly useful in the healthcare research environment, where subject matter experts should define the semantic conceptual mappings rather than information technology experts.

Exemplary illustrative embodiments also provide for a computer implemented method, apparatus, and computer usable program code for mapping data. A semantic conceptual mapping is defined. The semantic conceptual mapping is defined by a user and maps a source datum to a target datum having a target attribute. The semantic conceptual mapping is defined using metadata. Source specific information is omitted from the semantic conceptual mapping. The semantic conceptual mapping is stored in a target data repository.

Figure 3:
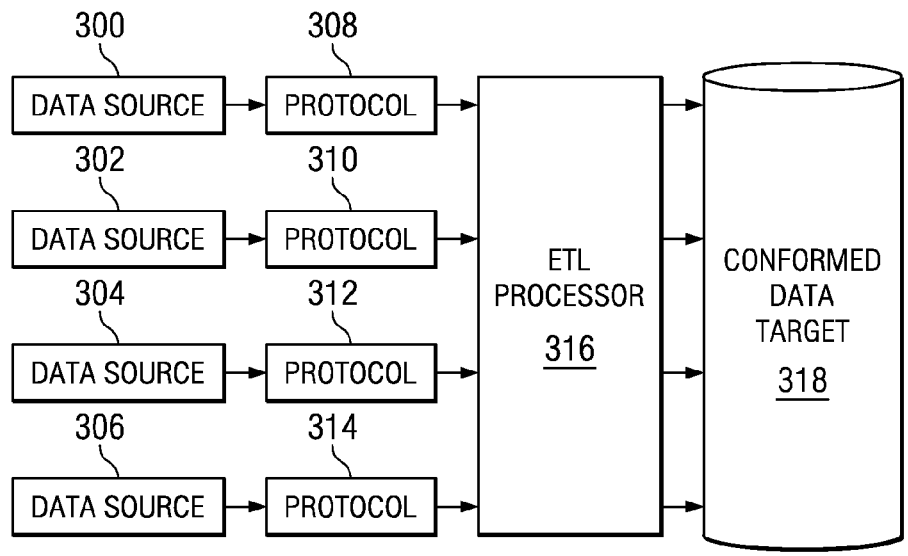
FIG. 3 is a block diagram illustrating a prior art extract, transform, and load process.

FIG. 3 is a block diagram illustrating a prior art extract, transform, and load process. The process shown in FIG. 3 can be implemented in a data processing system, such as servers 104 or 106, or clients 110, 112, or 114 shown in FIG. 1, or in data processing system 200 shown in FIG. 2. The process shown in FIG. 3 can be implemented among multiple computers transferring data over a network, such as network 102 shown in FIG. 1.

In the simplified extract, transform, and load process shown in FIG. 3, each data source 300, 302, 304, and 306 is extracted, transformed, and loaded via a separate corresponding protocol, such as protocols 308, 310, 312, and 314. Thus, for example, data source 300 is accessed and processed by extract, transform, and load (ETL) processor 316 via protocol 308, such that data source 300 is entered into conformed data target 318. Conformed data target 318 can be, for example, a unified database intended to hold data in a standardized format from each of data sources 300, 302, 304, and 306.

Each protocol 308, 310, 312, and 314 is built separately by information technology specialists. Additionally, even if data source 300 and data source 302 contain data relating to the same semantic concept, protocol 308 and protocol 310 may be very different from each other because data source 300 and data source 302 may use different naming conventions, data structures, operating systems, computer types, and may have many other differences.

For example, data source 300 and data source 302 each contain data relating to patient name and age. Thus, data source 300 and data source 302 refer to the same semantic concept—patient name and age. However, in this example, patient names in data source 300 are listed by last name and then first name, whereas patient names in data source 302 list names by fname (first name), mname (middle name), and lname (last name). Similarly, patient ages in data source 300 are in months format and patient ages in data source 302 are in year format. Additionally, data source 300 stores information in a simple table formatted for use with a UNIX® operating system, whereas data source 302 stores information in a relational database, having a different data model, wherein the relational database is designed for use with a WINDOWS® operating system. Thus, while data source 300 and data source 302 refer to the same semantic concept, data source 300 is not semantically equivalent to data source 302.

This semantic inequality leads to the requirement that protocol 308 be different than protocol 310 when extract, transform, and load processor 316 is to transfer data from data sources 300 and 302 to conformed data target 318. Due to the technically difficult nature of creating protocols 308 and 310, information technology specialists design these protocols. However, such specialists may not be available, and when available, are expensive to hire. Additionally, subject matter experts, such as the clinical researchers, do not control the mappings from data sources 300, 302, 304, and 306 to conformed data target 318. As a result, conformed data target 318 may not be optimally arranged from the point of view of the subject matter experts, or may lack properties or elements desired by the subject matter experts. This problem is described further with respect to FIG. 4.

Figure 4:
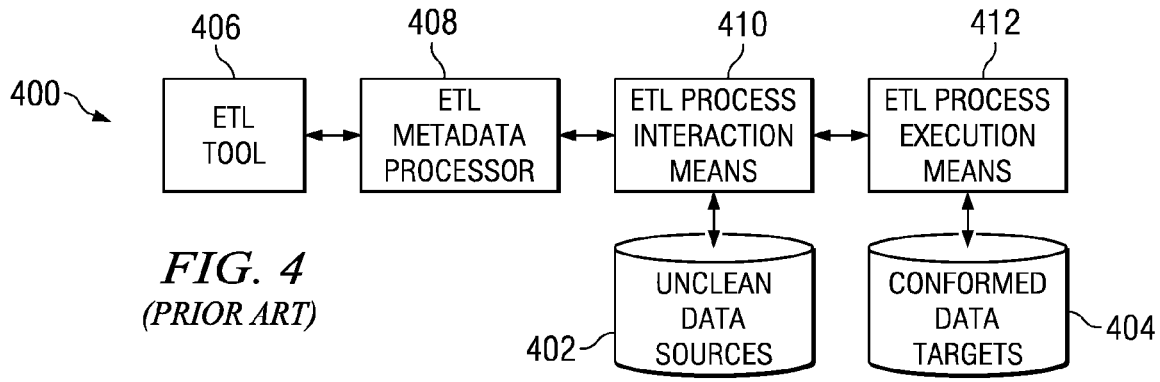
FIG. 4 is a block diagram illustrating a prior art extract, transform, and load process.

FIG. 4 is a block diagram illustrating a prior art extract, transform, and load process. The process shown in FIG. 4 can be implemented in a data processing system, such as servers 104 or 106, or clients 110, 112, or 114 shown in FIG. 1, or in data processing system 200 shown in FIG. 2. The process shown in FIG. 4 can be implemented among multiple computers transferring data over a network, such as network 102 shown in FIG. 1. Process 400 is a different version or manner of presenting process 300 shown in FIG. 3.

Extract, transform, and load (ETL) process 400 in FIG. 4 is used to transfer data from unclean data sources 402 to conformed data targets 404. A data source is unclean if the data source does not conform with or has not been verified to conform with a data target. A data source is also unclean if the data source is not semantically equivalent to a data target.

A data source can be a database, a text file, an image file, an audio file, or any other form of data. Similarly, a data target can be a database, a text file, a picture file, an audio file, or any other form of data. In the illustrative examples herein, a data target stores data in one or more preferred data formats and one or more preferred semantic formats. A data format is a data structure or format for storing data. A semantic format is how a data object is presented or stored. For example, a data format can be a simple text file or a database. A semantic format can be age in months or age in years.

Unclean data sources 402 stores data in legacy formats which often do not comport with the desired data formats in conformed data targets 404. The term conformed data targets means that the data targets are conformed to the desired data format.

Extract, transform, and load (ETL) tool 406 is used to perform the extraction, transformation and loading of data from unclean data sources 402 to conformed data targets 404. Extract, transform, and load tool 406 is an available tool that can be purchased from vendors, such as International Business Machines Corporation. Examples of extract, transform, and load tools include DB2™ for metadata repository, Ascential™ for ETL provisioning, Infomatica PowerMart™, Pervasive DJCOSMOS™, and J2E™ based struts framework.

Extract, transform, and load metadata tool 406 interacts with extract, transform, and load metadata processor 408 in that extract, transform, and load tool 406 is used to establish how extract, transform, and load metadata processor 408 will work. Extract, transform, and load metadata processor 408 can be one or more data processing systems, such as servers 104 or 106, or clients 110, 112, and 114 in FIG. 1, or data processing system 200 in FIG. 2. However, extract, transform, and load metadata processor 408 can also be implemented using software. Extract, transform, and load metadata processor 408 and extract, transform, and load process interaction means 410 represent a handcrafted extract, transform or load process or plan for transforming data from unclean data sources 402 to conformed data targets 404.

In the prior art process shown in FIG. 4, extract, transform, and load metadata processor 408 process metadata for use with extract, transform, and load process interaction means 410. Metadata is data that is associated with or describes other data. For example, a datum of interest could be a patient name, metadata describing that datum could be a date stamp of the datum, a data format of the datum, a semantic format of the datum, an author of the datum, the time the datum was last accessed, a last time a target loaded, or data describing any other desired property of the datum of interest.

Extract, transform, and load processor 408 creates or accesses metadata so that extract, transform, and load processes interaction means 410 can access unclean data sources 402 in the desired manner and allow extract, transform, and load process execution means 412 to perform the extraction, transformation, and loading of data in the proper manner. For example, extract, transform, and load metadata processor 408 can create or access metadata regarding a data format of a datum of interest in a source. Extract, transform, and load process interaction means 410 can then use that metadata to allow extract, transform, and load execution means 412 to transform the data format from the legacy format in unclean data sources 402 into the desired format in conformed data targets 404. However, as described above with respect to FIG. 3, extract, transform, and load processor 408 and extract, transform, and load interaction means 410 rely on handcrafted protocols designed by information technology specialists.

Extract, transform, and load process interaction means 410 can be a data processing system, such as servers 104 and 106, or clients 110, 112, or 114 as shown in FIG. 1, or data processing system 200 shown in FIG. 2. Extract, transform, and load interaction means 410 can also be implemented using software. Extract, transform, and load process interaction means 410 interacts with extract, transform, and load metadata processor 408 to retrieve data from unclean data sources 402 and provide such data in a desired order and manner to extract, transform, and load process execution means 412.

Extract, transform, and load process execution means 412 can be one or more data processing systems, such as servers 104 or 106, or clients 110, 112, or 114 in FIG. 1, or data processing system 200 shown in FIG. 2. Extract, transform, and load execution means 412 can also be implemented using software. Extract, transform, and load process execution means 412 actually performs the process of extracting, transforming and loading data from unclean data sources 402 to data targets 404.

Although the process shown in FIG. 4 can be used to extract, transform, and load data from unclean data sources 402 to data targets 404, process 400 suffers from numerous disadvantages. Exemplary disadvantages include the fact that process 400 has to be handcrafted for the particular project at hand, only information technology specialists with limited subject matter expertise in the desired research field can create and then execute process 400, and process 400 cannot be reused for other extract, transform, and load processes.

Figure 5:
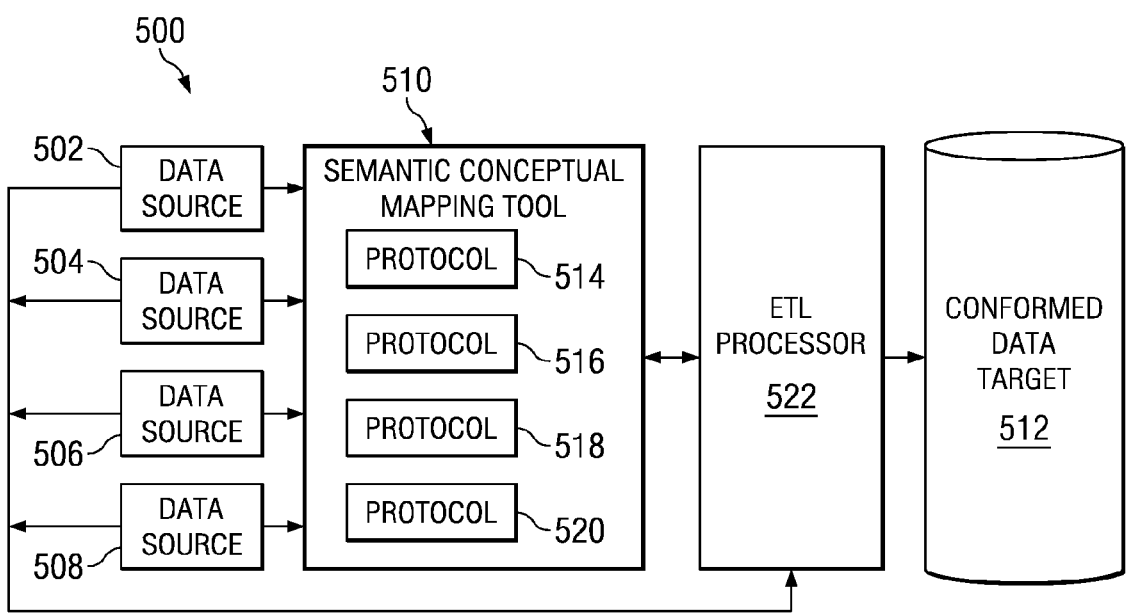
FIG. 5 is a block diagram of an extract, transform, and load process using metadata mapping to capture semantic concept mappings, in accordance with an illustrative embodiment.

FIG. 5 is a block diagram of an extract, transform, and load process using metadata mapping to capture semantic concept mappings, in accordance with an illustrative embodiment. Process 500 shown in FIG. 5 is similar to process 300 shown in FIG. 3. However, process 500 solves the problems described above with respect to the prior art method shown in FIG. 3 and FIG. 4. Process 500 can be implemented using one or more data processing systems, such as server 104 and 106, or clients 110, 112, and 114 shown in FIG. 1, or data processing system 200 shown in FIG. 2.

Unlike process 300 shown in FIG. 3, process 500 does not rely on information technology specialists to hand craft different protocols for each different data source. Instead, data sources 502, 504, 506, and 508 are accessed by semantic conceptual mapping tool 510. A person who is not an information technology specialist can operate semantic conceptual mapping tool 510 to specify a semantic conceptual mapping from each of data sources 502, 504, 506, and 508 to conformed data targets 512.

Semantic conceptual mapping tool then uses metadata mapping, as described further below, to automatically establish protocols 514, 516, 518, and 520. In particular, metadata regarding the source is mapped to corresponding metadata with respect to the target. Based on this metadata mapping, an appropriate extract, transform, and load protocol can be created automatically. An important difference between the prior art methods shown in FIG. 3 and FIG. 4 and the process shown in FIG. 5 is that metadata in the prior art methods is created and/or manipulated using protocols created by information technology specialists. However, in the process shown in FIG. 5, the source metadata is first mapped to desired target metadata and the protocols are established later as a natural result of that mapping.

Extract, transform, and load processor 522 can then interact with semantic conceptual mapping tool 510 via protocols 514, 516, 518, and 520 and with data sources 502, 504, 506, and 508 to an extract, transform, and load process. This extract, transform, and load process will transfer data from data sources 502, 504, 506, and 508 to conformed data target 512, such that the data in the data sources is in a desired data format and a desired semantic format for objects semantically mapped.

Because semantic conceptual mapping tool 510 creates protocols 514, 516, 518, and 520 based on semantic conceptual mappings specified using a graphical user interface, or other means for specifying a semantic conceptual mapping, such as text or a table, no particular expertise is required to create process 500. Thus, subject matter experts, such as clinical researches, can create process 500 and avert many of the difficulties associated with the prior art processes shown with respect to FIG. 3 and FIG. 4.

Figures 6, 8:
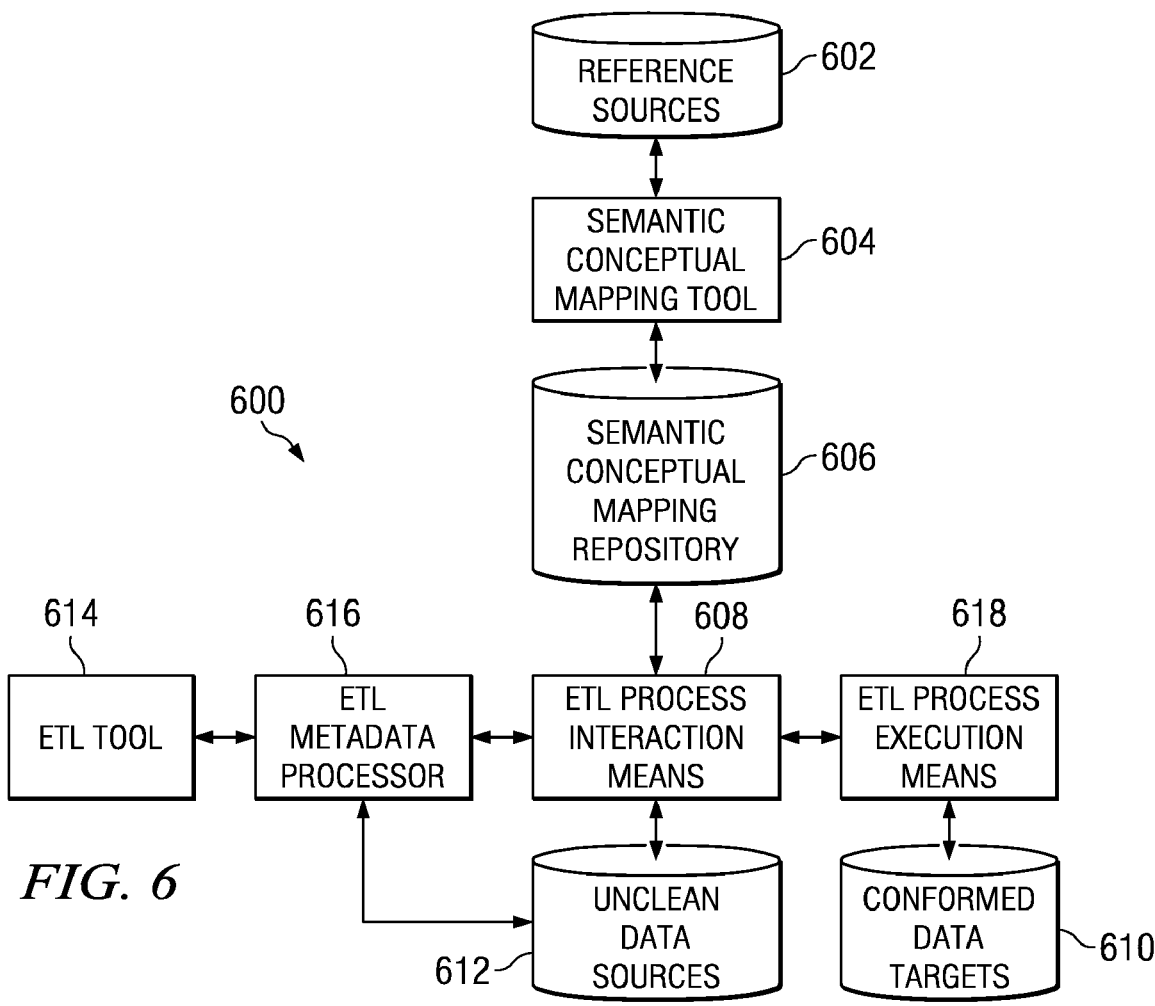
FIG. 6 is a block diagram of a process for using a semantic conceptual mapping tool to perform an extract, transform, and load process, in accordance with an illustrative embodiment.
FIG. 8 is a table showing an exemplary semantic conceptual mapping from source attributes to target domains, in accordance with an illustrative embodiment.

FIG. 6 is a block diagram of an extract, transform, and load process using metadata semantic conceptual mapping, in accordance with an illustrative embodiment. Process 600 shown in FIG. 6 is similar to process 500 shown in FIG. 5. Process 600 is a different version or manner of presenting process 500 shown in FIG. 5. Process 600 can be implemented using one or more data processing systems, such as server 104 or 106, or clients 110, 112, or 114 shown in FIG. 1, or data processing system 200 shown in FIG. 2.

In the exemplary embodiment shown in FIG. 6, semantic conceptual mapping tool 604 interacts with reference sources 602 and semantic conceptual mapping repository 606. Reference sources 602 can be data dictionaries, online resources, such as SNOMED, ICD6 through ISC9, LOINC, custom vocabularies created for process 600, code lists, semantic rules, or other references. Semantic conceptual mapping tool 604 uses these references to create a semantic conceptual mapping between a source datum and a target domain, wherein the semantic conceptual mapping is implemented using metadata.

A target domain is a data structure, in which semantically similar information is stored. Thus, for example, an age datum expressed in months and an age datum expressed in years are semantically similar and are both mapped to a target domain of age. As shown further below, domains can also be organized into groups. For example, an age target domain, a gender target domain, and an ethnicity target domain can be organized into a broader demographics super domain.

As described above, semantic conceptual mapping tool 604 uses these references to create a semantic conceptual mapping between a source datum and a target domain. This semantic conceptual mapping can be referred to as a semantic conceptual construct. The semantic conceptual construct is stored in a repository, such as semantic conceptual mapping repository 606. One of the many advantages of the process shown in FIG. 6 is that extract, transform, and load process interaction means 608 can access semantic conceptual constructs stored in semantic conceptual mapping repository 606. Thus, once the semantic conceptual constructs are created, they can be used and reused as desired.

Semantic conceptual mapping repository 606 interacts with extract, transform, and load process interaction means 608. The exemplary embodiments described herein can interact with existing extract, transform, and load tools, such as extract, transform, and load tool 614. Semantic conceptual mapping tool 604 can be used by subject matter experts, such as clinical researchers that have limited information technology knowledge, as opposed to only information technology specialists. The term "limited information technology knowledge" means that the individual in question lacks the knowledge to create a known extract, transform, and load process, such as that shown in FIG. 3 or FIG. 4.

As also described above, semantic conceptual mapping tool 604 is used to specify a semantic conceptual mapping of a data object from unclean data sources 612 to a data object in conformed data targets 610. This mapping is a semantic conceptual construct. The semantic conceptual construct particularly maps a source datum to a target domain. Semantic conceptual mapping tool 604 then determines, using metadata, what actions will be needed to actually perform the extract, transform, and load of the data object from the unclean data source to the conformed data target. This semantic conceptual mapping is then repeated for each additional data object to be extracted, transformed and loaded. The semantic conceptual mappings are stored in semantic conceptual mapping repository 606. Semantic conceptual mappings can be defined using extensible markup language (XML), a database schema, or other well known technical means. Thereafter, the actual extraction, transformation and loading from unclean data sources 612 to conformed data targets 610 proceeds according to normal extract, transform, and load processes.

Thus, the illustrative embodiments described herein capture the rules used for a semantic level equivalency mapping between unclean data sources 612 and conformed data targets 610. More specifically, semantic conceptual mapping tool 604 captures the rules needed for semantic level equivalency mapping between source data and the defined target domain based attributes established for population in conformed data targets 610.

Once the semantic conceptual mapping definition is complete and the semantic conceptual constructs created, semantic conceptual mapping tool 604 can trigger the process of moving source data from unclean data sources 612 to conformed data targets 610. In an illustrative embodiment, the semantic conceptual mapping is performed once the semantic conceptual mapping has been shown to be valid. This rule can act as an on/off trigger for extract, transform, and load tool 614. In this embodiment, only valid and complete semantic conceptual mappings are usable by the extract, transform and load means.

In an illustrative embodiment, movement of the data is prohibited prior to the completion of the semantic conceptual mapping in order to prevent uncleansed data from contaminating conformed data targets 610. As described above, the actual extract, transform, and loading process remains under the control and domain of extract, transform, and load tool 614, extract, transform, and load metadata processor 616 and extract, transform, and load execution means 618, which can all be implemented using known techniques, software, and hardware.

Figure 7:
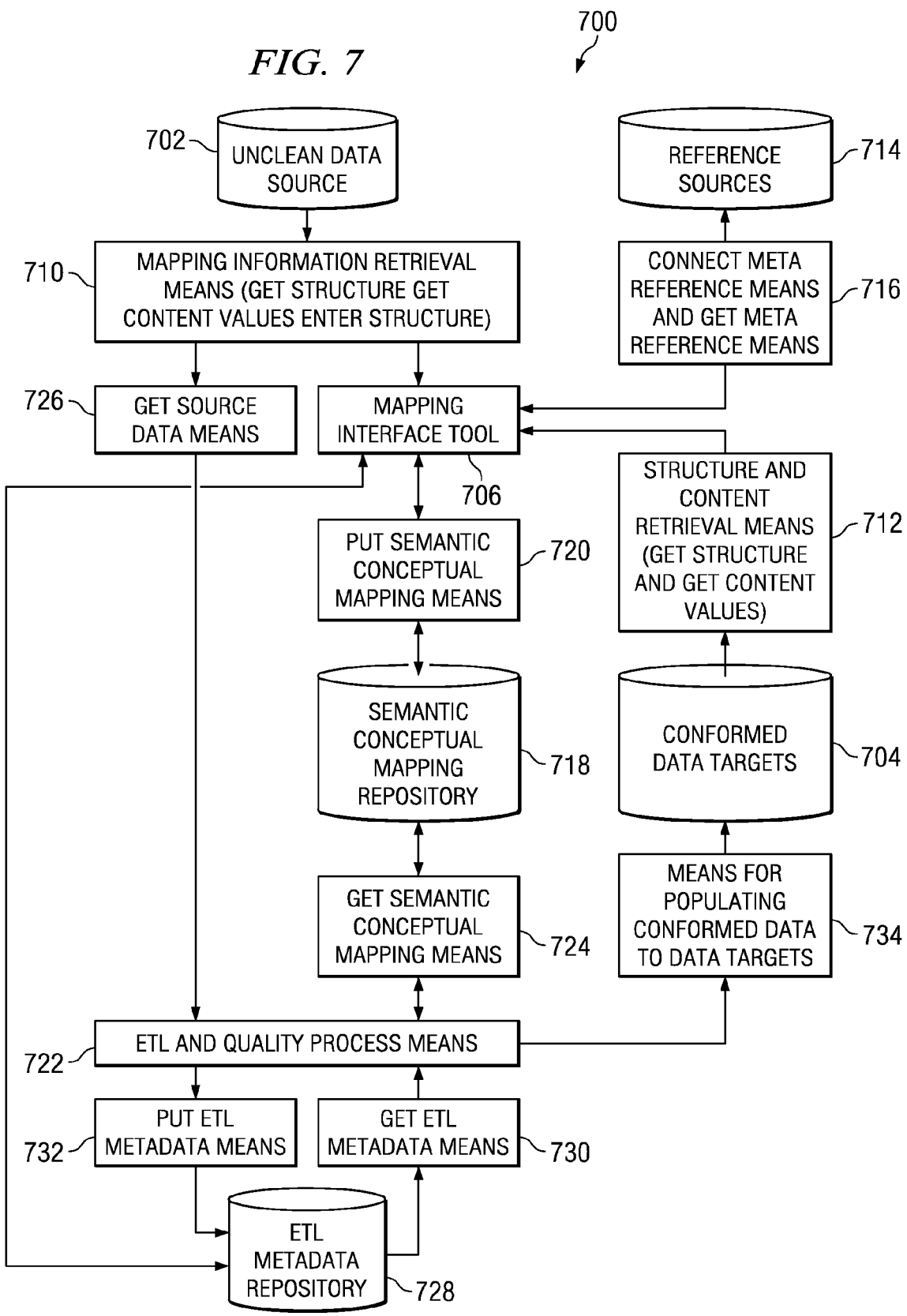
FIG. 7 is a block diagram of a process for using a semantic conceptual mapping tool to perform an extract, transform, and load process, in accordance with an illustrative embodiment.

FIG. 7 is a block diagram of a process for using a semantic conceptual mapping tool to perform an extract, transform, and load process, in accordance with an illustrative embodiment. Process 700 shown in FIG. 7 is another illustrative example of using a semantic conceptual mapping tool, such as semantic conceptual mapping tool 604 shown FIG. 6. Process 700 shown in FIG. 7 shows more details with respect to operation of semantic conceptual mapping tool 604 of FIG. 6. Process 700 shown in FIG. 7 can be implemented using one or more data processing systems, such as servers 104 and 106, or clients 110, 112, and 114 shown in FIG. 1, or data processing system 200 shown in FIG. 2.

As with process 600 shown in FIG. 6, process 700 shown in FIG. 7 is used to extract, transform, and load from unclean data source 702 to conformed data targets 704. Process 700 is planned and initiated using mapping interface tool 706, which corresponds to semantic conceptual mapping tool 604 shown in FIG. 6. Similarly, semantic conceptual mapping repository 718 corresponds to semantic conceptual mapping repository 606 shown in FIG. 6.

In process 700, mapping interface tool 706 receives user-defined mappings from one or more data objects in unclean data source 702 to one or more data objects in conformed data targets 704. Thereafter, mapping interface tool 706 receives data structures and content values from unclean data source 702 via mapping information retrieval means 710. Mapping information retrieval means 710 can be software or a data processing system, such as servers 104 and 106, or clients 110, 112, and 114 shown in FIG. 1, or data processing system 200 shown in FIG. 2

Similarly, mapping interface tool 706 receives data structures and content values from conformed data targets 704 via structure and content retrieval means 712. Structure and content retrieval means 712 can be software or one or more data processing systems, such as servers 104 and 106, or clients 110, 112, and 114 shown in FIG. 1, or data processing system 200 shown in FIG. 2

Mapping interface tool 706 also obtains desired or required reference information from one or more reference sources, such as reference sources 714. Reference sources 714 can be data dictionaries, online resources, such as SNOMED, ICD6 through ISC9, LOINC, custom vocabularies created for process 700, lookup tables, code lists, semantic rules, or other references. Reference sources 714 can also contain metadata describing source data. Mapping interface tool 706 uses these references to create a metadata mapping between a source datum and a target domain. Mapping interface tool 706 obtains reference data from reference sources 714 via connect meta-reference means and get meta-reference means 716. Connect meta-reference means and get meta-reference means 716 can be one or more data processing systems, one or more software systems, or other means for connecting and retrieving information.

Mapping interface tool 706 then transmits semantic conceptual constructs, which are metadata mappings, to semantic conceptual mapping repository 718 via put semantic conceptual mapping means 720. Put conceptual mapping means 720 can be software or one or more data processing system, such as servers 104 and 106, or clients 110, 112, and 114 shown in FIG. 1, or data processing system 200 shown in FIG. 2. In this manner, semantic conceptual mapping repository 718 stores a number of semantic conceptual mappings from unclean data source 702 to conformed data targets 704.

At this stage, semantic conceptual mapping repository 718 interacts with extract, transform, and load and quality process means 722 via get semantic conceptual mapping means 724. Extract, transform, and load and quality process means 722 can be any currently available tool or means for performing extract, transform, and loading and quality control, such as extract, transform, and load processor 316 shown in FIG. 3. Get semantic conceptual mapping means 724 can be software or one or more data processing systems, such as servers 104 and 106, or clients 110, 112, and 114 shown in FIG. 1, or data processing system 200 shown in FIG. 2. Get semantic conceptual mapping means 724 allows extract, transform, and load and quality process means 722 to receive semantic conceptual constructs from semantic conceptual mapping repository 718.

Extract, transform, and load and quality process means 722 also retrieves data objects from unclean data source 702 via get source data means 726 and mapping information retrieval means 710. Additionally, extract, transform, and load and quality process means 722 retrieves desired or required metadata from extract, transform, and load metadata repository 728 via get extract, transform, and load metadata means 730. During this process, put extract, transform, and load metadata means 732 is used to place additional metadata or metadata created during the extract, transform, and load process into extract, transform, and load metadata repository 728.

After or during performing the extract, transform, and load process, extract, transform, and load and quality process means 722 populates transform data objects to conformed data targets 704 via means for populating conformed data to data targets 734. As used herein, get source data means 726, get extract, transform, and load metadata means 730, put extract, transform, and load metadata means 732, and means for populating conformed data to data targets 734 can all be software or one or more data processing systems, such as servers 104 and 106, or clients 110, 112, and 114 shown in FIG. 1, or data processing system 200 shown in FIG. 2.

Mapping interface tool 706 can provide the metadata to drive the dynamic and adaptive extract, transform, and load processes described in FIG. 7. Mapping interface tool 706 allows the mapping of trial data captured for one specific trial or study to be automatically and accurately combined with other studies and trials for the relevant data domains that are mapped. Thus, mapping interface tool 706 enables cross-trial analysis in clinical research studies.

Additionally, a subject matter expert will be able to capture and program a set of semantic conceptual constructs to support the normalization and/or mapping of source data attributes into target domains. As described above, a semantic conceptual mapping or semantic conceptual construct is a mapping from a first data object to a second data object, wherein metadata specify the structure and semantics of the first data object, the second data object, and the semantic conceptual mapping. Metadata is data which describes another set of data.

In one illustrative example, a semantic conceptual construct specifies how a target set of data is to be mapped into conformed data targets 704. Semantic conceptual constructs stored in semantic conceptual mapping repository 718 can interact with standardized extract, transform, and load packages or processes to support population of standard target domains. Thus, the illustrative embodiments described herein ensure that all existing and new clinical data will be loaded in a consistent and semantically equivalent manner into conformed data targets, such as conformed data targets 704, without requiring an information technology specialist to perform the actual mapping.

Additionally, mapping interface tool 706 provides an interface to support various types of semantic conceptual mapping. An example of a semantic conceptual mapping supported by mapping interface tool 706 is alias resolution. In alias resolution, the mapping definition for a source attribute name to a target attribute name is provided. An example of alias resolution is mapping the term "DIAG" to the term "DIAGNOSIS". Alias resolution can be performed on a source-by-source basis.

Another type of semantic conceptual mapping is code standardization. Code standardization supports the definition of mapping source code list to the standard target domain attribute code name list. An example of code standardization is mapping of age to age ranges or mapping ICD9 to ICD10, which are medical billing coding standards.

Another type of semantic conceptual mapping is transforming numerical calculated values to other units of numerical calculated values. For example, measurements could be transformed from metric to imperial or from one type of unit to another type of unit.

Another type of semantic conceptual mapping is format resolution. Format resolution ensures that source formats conform to target domain attribute formats. An example of format resolution is changing dates in the form of month/day/year to the long form of month, day, year.

Another type of semantic conceptual mapping is standardization of dictionaries and terms. For example, names of drugs in clinical terminology can be mapped to a common type of name. For example, different brand name drugs can be mapped to the generic terms for those same drugs. Similarly, a term, such as bruise, could mapped to the term hematoma.

Thus, the illustrative embodiments described herein semantically maps data into forms, such that the data are consistently identifiable and classified. Metadata is created or updated which is domain specific. Associated ontologies and taxonomies are identified with data domains.

In an illustrative example, conformed data targets 704 is a database in which data is stored in a semantically equivalent fashion at the atomic level. All levels of granularity are conformed based on dimensions to ensure uniform meaning in queries. Conforming of levels of granularity based on dimensions is achieved by consistent integration facilitated by capture of semantic equivalence via metadata. Thus, queries can be written against every level of aggregation of data without a user having to know about underlying details of the extract, transform, and load process. Additionally, aggregations of data will be produced during the transform stage of extract, transform, and load process even if the aggregations did not exist in the underlying data source. Aggregations of data include subtotals and totals, mathematical means, modes, standard deviations, maximum values, minimum values, and other standard statistical computations. Aggregations of data support more rapid report generation and manual report analysis.

Thus, the illustrative embodiments described herein provide a conformed information space in which users who have limited information technology knowledge can query the database of conformed data targets 704 without ongoing direct programming support.

FIG. 8 is a table showing an exemplary semantic conceptual mapping from source attributes to target domains, in accordance with an illustrative embodiment. The table shown in FIG. 8 can be implemented as software or hardware in a data processing system, such as data clients 104 and 106 or servers 110, 112, and 114 in FIG. 1, or data processing system 200 shown in FIG. 2. The table shown in FIG. 8 is an example of semantic conceptual mapping of a source element to a target domain, as described with respect to FIG. 5 through FIG. 7.

Table 800 shows a number of source elements in source attribute column 802 and a number of target domains in target domain column 804. A source element can be any aspect of interest of a source data or metadata associated with a source data. Table 800 shows a number of source elements, such as source element 806, source element 808, source element 810, source element 812, and source element 814.

Each source element has a corresponding target domain in target domain column 804. A target domain is a semantic concept into which a source attribute will fit. Table 800 shows that source element 806 is semantically mapped to "procedure text" domain 816, source element 808 is semantically mapped to "procedure-row" domain 818, and source elements 810, 812, and 814 are semantically mapped to procedures 820, 822, and 824, respectively. As used with respect to FIG. 8, a procedure is a procedure relating to a source.

FIG. 9 is a table showing an exemplary semantic conceptual mapping from source attributes to target domains, organized by subtype, in accordance with an illustrative embodiment. The table shown in FIG. 9 can be implemented as software or hardware in a data processing system, such as data clients 104 and 106, or servers 110, 112, and 114 in FIG. 1, or data processing system 200 shown in FIG. 2. The table shown in FIG. 9 is an example of semantic conceptual mapping, and at a detailed exemplary level, a source element to a target domain, as described with respect to FIG. 5 through FIG. 9. Thus, FIG. 9 is a detailed example of conceptual table 800 shown in FIG. 8.

Table 900 includes a number of source attributes in source attribute column 902 and target domain column 904. Examples of source attributes include "DOB 906, "M or F" 908, "ethnicity" 910, "BMI" 912, "HT" 914, "Age in Months" 916, and source attributes 918, 920, and 922.

Source attributes correspond to various target domains. Some source attributes map to the same target domain because the source attributes are conceptually equivalent. Thus, for example, both source attribute "DOB" 906 and source attribute "Age in Months" 916 map to target domain "Age" 924. Other source attributes are to be mapped to two different target domains. For example, two instances of source attribute "BMI" 912 are shown. In this example, because of the researcher's desire, source attribute "BMI" 912 is mapped to target domain "BMI Metric" 926 and target domain "BMI in text" 928.

Other semantic conceptual mappings are shown. For example, source attribute "M or F" 908 maps to target domain "Gender" 930, source attribute "Ethnicity" maps to target domain "Ethnic Origin" 932, source attribute "HT" 914 maps to target domain "Height in Metric" 934 and source attributes 918, 920, and 922 map to corresponding target domains "Drug Name" 936, "Drug Class" 938, and "Dosage" 940.

Target domains can also be categorized into super target domains. A super domain is a group of target domains. For example, target domains "Age" 924, "Gender" 930, "Ethnic Origin" 932, "BMI Metric" 926, "BMI in Text" 928, and "Height in Metric" 934 are all a part of super domain "Demographic" 942. Likewise, target domains "Drug Name" 936, "Drug Class" 938, and "Dosage" 940 are all a part of super domain "Drugs" 944

In the illustrative examples described herein, a semantic conceptual mapping tool is used to map a source attribute to a target domain using metadata. Thus, a semantic conceptual mapping tool can be used to specify the semantic conceptual mappings and super domains shown in table 900 of FIG. 9. After being specified, the semantic conceptual mapping tool constructs semantic conceptual constructs to implement the semantic conceptual mappings from the source attributes to the corresponding target domains. An example of such a semantic conceptual mapping process is shown with respect to FIG. 10.

FIG. 10 is a table showing an exemplary semantic conceptual mapping from source data to target data using a semantic mapping rule, in accordance with an illustrative embodiment. The table shown in FIG. 10 can be implemented as software or hardware in a data processing system, such as data clients 104 and 106 or servers 110, 112, and 114 in FIG. 1, or data processing system 200 shown in FIG. 2. The table shown in FIG. 10 is an example of mapping a source data to a conformed data target, as described with respect to FIG. 5 through FIG. 10. In particular, table 1000 shows source datum to conformed target data mappings using semantic mapping rules derived from semantic conceptual mappings specified in table 900 shown in FIG. 9.

Table 1000 shows three columns, source datum column 1002, conformed target data column 1004, and semantic mapping rule column 1006. The rows shown have been organized into domains. In the example of table 1000, "Demographics:Gender" domain 1008 refers to super domain "Demographics" 942 and target domain "Gender" 930 in FIG. 9. Within domain 1008 a number of different source data attribute values are shown, including 0, 1, and "-". The source data is to be semantically mapped to the terms as shown; specifically, 0 maps to "Male," 1 maps to "Female," and "-" maps to "Unknown." In each case, the semantic mapping rule is "number gender conversion" 1012. This semantic mapping rule can be embodied as a semantic conceptual construct created using a semantic conceptual mapping tool, such as those shown with respect to FIG. 5 through FIG. 7.

A similar process can apply with respect to "Demographics:Age" target domain 1012. In this example, two semantic mapping rules are used, "Months Age conversion" 1014 and "DOB Age Conversion" 1016. These semantic mapping rules can be implemented as semantic conceptual constructs created by using a semantic conceptual mapping tool, such as those shown with respect to FIG. 5 through FIG. 7. Thus, source data 480 can be mapped to conformed data target 40 using "Months Age Conversion" 1014 and source data Jan. 1, 1970 can be mapped to conformed data target 37 using "DOB Age Conversion" 1016.

Figure 11:
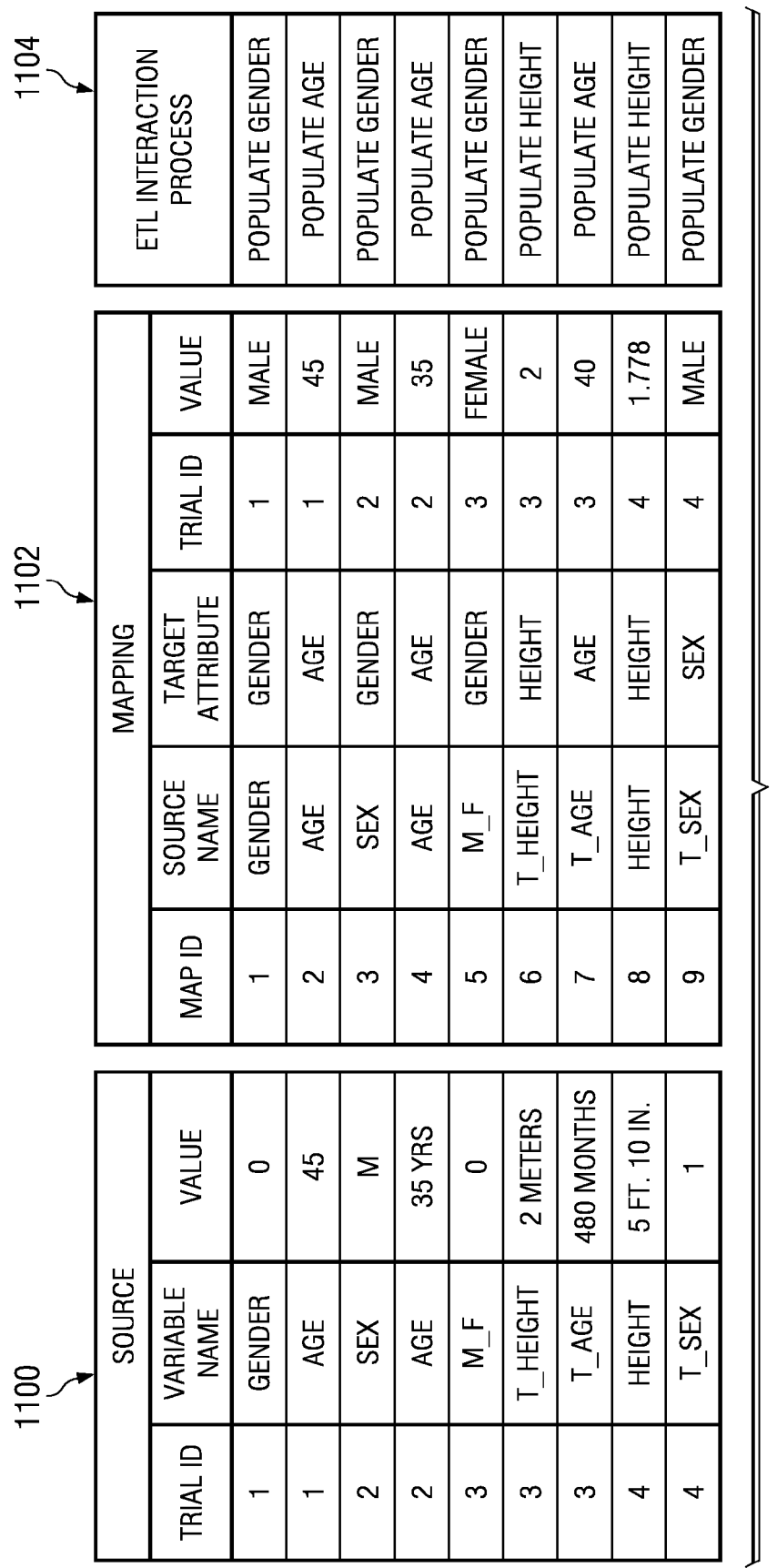
FIG. 11 is a table of an exemplary source, semantic conceptual mapping, and extract, transform, and load interaction process, in accordance with an illustrative embodiment.

FIG. 11 is a table of an exemplary source, semantic conceptual mapping, and extract, transform, and load interaction process, in accordance with an illustrative embodiment. Tables shown in FIG. 11 can be implemented in one or more data processing systems, such as servers 104 and 106, or clients 110, 112, and 114 shown in FIG. 1, or data processing system 200 shown in FIG. 2. Source 1100 can be considered to be an unclean data source, such as unclean data sources 402 in FIG. 4. Semantic conceptual mapping 1102 shows the semantic conceptual mappings to be performed between, for example, unclean data source 402 and conformed data targets 404 in FIG. 4. Semantic conceptual mapping 1102 shows examples of semantic conceptual constructs which can be stored in semantic conceptual mapping repository, such as semantic conceptual mapping repository 606 shown in FIG. 6 and semantic conceptual mapping repository 718 shown in FIG. 7. Extract, transform, and load process 1104 is a table of commands, which can be used by an extract, transform, and load process and interaction means, such as extract, transform, and load process interaction means 410 shown in FIG. 4.

In the illustrative example shown in FIG. 11, data in source 1100 is mapped using semantic conceptual mapping 1102 according to extract, transform, and load interaction process 1104. The resulting transformations are stored in a conformed data target repository, such as conformed data targets 404 shown in FIG. 4. For example, source 1100 shows a trial ID (identification) of 3 for variable name M_F with a value of 0. The mapping ID in semantic conceptual mapping 1102 corresponds to a source name of M_F, a target attribute of gender, a trial ID of 3, and a value of female. Extract, transform, and load process 1104 will then execute a process to populate a gender attribute in a conformed data target, such as conformed data targets 404 shown in FIG. 4. The remaining data objects in source 1100 are mapped according to semantic conceptual 1102 using extract, transform, and load process 1104 as shown in FIG. 11.

FIG. 12 is a flowchart illustrating a method of semantic conceptual source data to a domain attribute using metadata, in accordance with an illustrative embodiment. The process shown in FIG. 12 can be implemented in one or more data processing systems, such as servers 104 and 106, or clients 110, 112, and 114 shown in FIG. 1, or data processing system 200 shown in FIG. 2. The process shown in FIG. 12 can be implemented in a semantic conceptual mapping tool, such as semantic conceptual mapping tool 510 shown in FIG. 5, or semantic conceptual mapping tool 604 shown in FIG. 6.

The process begins as the semantic conceptual mapping tool receives a semantic conceptual mapping definition (step 1200). A semantic conceptual mapping definition is often created by a user, but could be automatically generated. The semantic conceptual mapping tool then loads and populates a target definition (step 1202). A target definition is a data structure that defines how data is to be stored and the format of the data in a conformed data target. Target definitions are organized according to target domains. A target domain is a classification of data. For example, a target domain could be gender.

The process continues as the semantic conceptual mapping tool selects a target domain for creation of a metadata-based semantic conceptual mapping (step 1204). The semantic conceptual mapping tool then selects a particular domain attribute (step 1206). A domain attribute is a particular attribute of a domain. For example, a domain attribute could be the particular gender of male or female in the domain of gender.

The semantic conceptual mapping tool then determines a mapping type (step 1208). A mapping type can be considered a lookup value. For example, a user can look at "22MAY07"

and recognize the value as a date. A mapping type selects the type of mapping to take place. Typical mappings may include patient number, gender codes (Males vs. M vs. "1"), dates, weights (grams and kilograms vs. ounces and pounds), volumes (gallons vs. liters), lengths (meters and kilometers vs. feet and miles), and drug names to chemical names.

The semantic conceptual mapping tool then selects the next source variable (step 1210) and analyzes the field contents to deduce the data type in the source data field. The semantic conceptual mapping tool creates a mapping from the source domain attribute to a target domain attribute (step 1212). The semantic conceptual mapping tool then validates the attribute mapping (step 1214). By validating attribute mapping, the semantic conceptual mapping tool ensures that the semantic conceptual mapping is correct and can be later performed by an extract, transform, and load process.

The semantic conceptual mapping tool determines whether the attribute mapping is valid (step 1216). If the attribute mapping is not valid (a 'no' result to the determination at step 1216), then the process returns to step 1212 and repeats. However, if the attribute mapping is valid (a 'yes' result to the determination at step 1216), then the semantic conceptual mapping tool determines whether the target domain mapping is complete (step 1218). If the target domain mapping is not complete (a 'no' result to the determination at step 1218), then the process returns to step 1206 and repeats. However, if the target domain mapping is complete (a 'yes' determination to step 1218), then the semantic conceptual mapping tool saves the semantic conceptual mapping as a semantic conceptual mapping construct (step 1220). The semantic conceptual mapping can be saved in a semantic conceptual mapping repository, such as semantic conceptual mapping repository 606 shown in FIG. 6, in the form of a data structure. The saved semantic conceptual mapping can then be used later by a standard extract, transform, and load tool to perform a semantic conceptual mapping of an unclean data object to a conformed data target.

The semantic conceptual mapping tool optionally can generate a mapping report (step 1222). A mapping report describes the type of mapping generated for a target domain. The mapping report can also show mappings for multiple domains, show information related to whether mappings are valid, information regarding which mappings are not valid, and other desired information.

The semantic conceptual mapping tool determines whether any errors occurred during the mapping (step 1224). If no error occurred during the mapping, then the semantic conceptual mapping tool can optionally schedule the mapping to take place (step 1228). The actual mapping can be performed by an extract, transform, and load process, such as extract, transform, and load tool 406 via extract, transform, and load process interaction means 410 shown in FIG. 4. If errors do exist (a 'yes' determination to step 1224), then the semantic conceptual mapping tool generates an error report (step 1226). The error report can describe the errors that occurred along with other desired information. The process could then be terminated by the user or could be restarted at step 1200 where the clinical subject matter expert can retrieve the erroneous semantic conceptual mapping and correct the semantic conceptual mapping.

Returning to step 1228, the semantic conceptual mapping tool determines whether to select a new target domain (step 1230). If a new target domain is to be selected (a 'yes' determination to step 1230), then the process returns to step 1204 and repeats. However, if a new target domain is not to be selected (a 'no' determination to step 1230), then the process terminates.

Figure 13A:
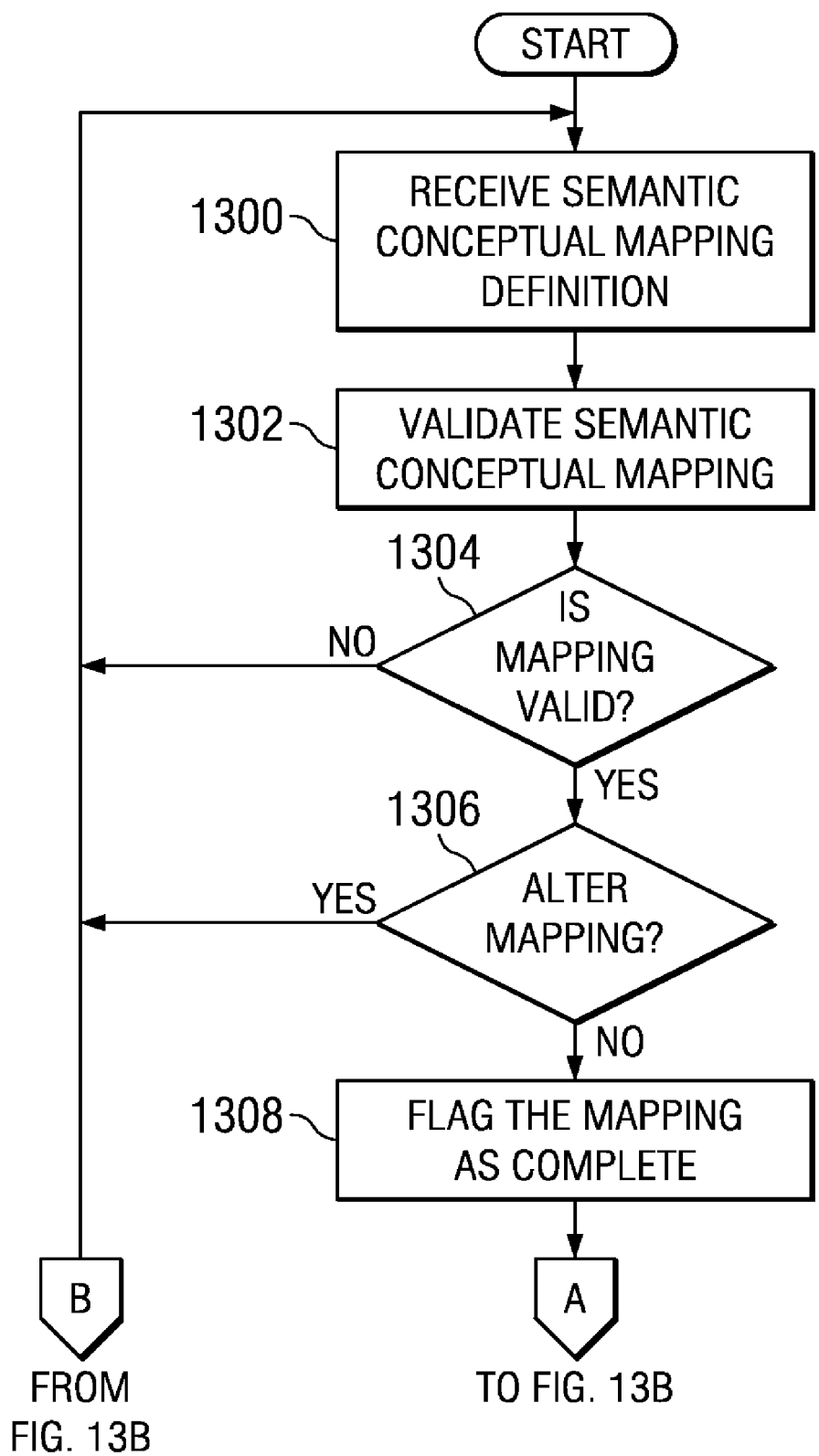
FIGS. 13A and 13B are a flowchart illustrating performing an extract, transform, and load process using a metadata-based semantic conceptual mapping, in accordance with an illustrative embodiment.
Figure 13B:
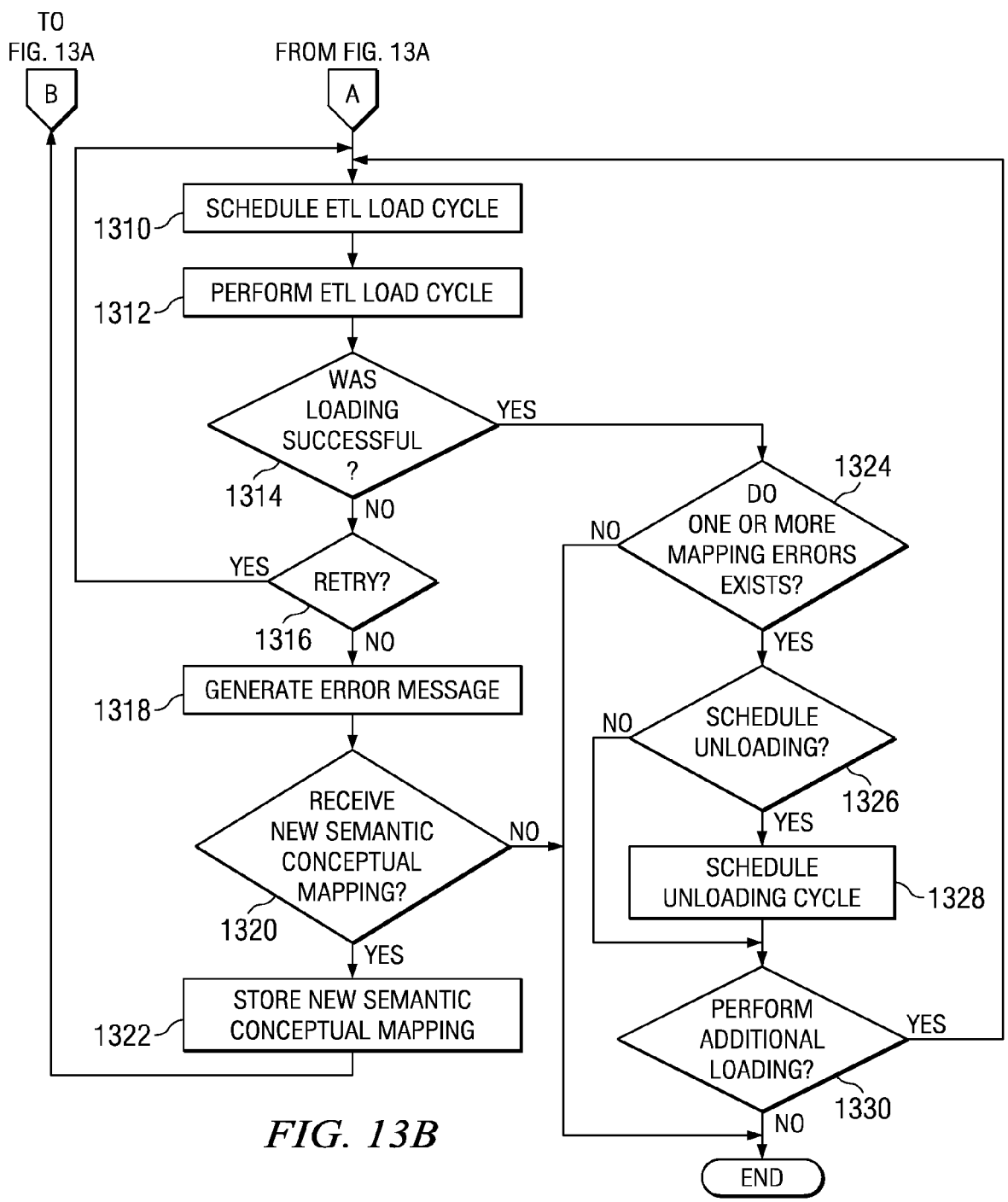

FIGS. 13A and 13B are a flowchart illustrating performing an extract, transform, and load process using metadata-based semantic conceptual mapping, in accordance with an illustrative embodiment. The process shown in FIGS. 13A and 13B can be implemented in a data processing system, such as servers 104 and 106, or clients 110, 112, and 114 shown in FIG. 1, or data processing system 200 shown in FIG. 2. The process shown in FIGS. 13A and 13B can be implemented using the combination of an extract, transform, and load tool, such as extract, transform, and load processor 522 shown in FIG. 5 or extract, transform, and load tool 614 in FIG. 6, and semantic conceptual mapping tool, such as semantic conceptual mapping tool 510 shown in FIG. 5, or semantic conceptual mapping tool 604 shown in FIG. 6. The process shown in FIGS. 13A and 13B is an overview of the entire process of using a semantic conceptual mapping tool to transform data from an unclean data source to a conformed data target.

The process begins as a semantic conceptual mapping tool receives a mapping definition (step 1300). The mapping definition can be created by a user. In particular, the mapping definition can be created by a subject matter expert, such as a clinician or other researcher who has limited information technology knowledge. The term "limited information technology knowledge" means that the individual in question lacks the knowledge to create a known extract, transform, and load process, such as that shown in FIG. 3 or FIG. 4.

The mapping definitions can be received via a graphical user interface, which allows a subject matter expert to easily specify a mapping from one type of data to a target type of data. The extract, transform, and load tool then validates the mapping (step 1302). A mapping is valid if the mapping complies with rules governing semantic conceptual constructs and rules established for the extract, transform, and load tool. The rules themselves are established by a variety of means, such as, but not limited to the manufacturer of the extract, transform, and load tool, a custom code library, an open-source community, or other relevant means.

The extract, transform, and load tool then determines whether the mapping is valid (step 1304). If the mapping is not valid (a 'no' determination to step 1304), then the process returns to step 1300 in order to receive a new mapping definition. If the mapping is valid (a 'yes' determination to step 1304), then the extract, transform, and load tool determines whether to alter the mapping (step 1306). A mapping could be altered responsive to user input to alter the mapping. The mapping could also be altered in response to rules or policies established in the semantic conceptual mapping tool. If mapping is to be altered (a 'yes' determination to step 1306), then the process returns to step 1300 to receive a new mapping definition that complies with the altered mapping definition. However, after a 'no' determination to step 1306, the semantic conceptual mapping tool flags the mapping as complete (step 1308).

At this point, control of the process is turned over to an extract, transform, and load tool, such as extract, transform, and load tool 406 described in FIG. 4. The extract, transform, and load tool schedules an extract, transform, and load cycle (step 1310). An extract, transform, and load cycle is a process for transforming unclean data sources to conformed data targets, as described with respect to FIG. 4. Scheduling of an extract, transform, and load cycle is often desired or necessary because such cycles can use a large amount of data processing resources and require significant time.

The extract, transform, and load tool then performs the extract, transform, and load cycle (step 1312). After performing the extract, transform, and load cycle, the extract, transform, and load tool determines whether the extract, transform, and loading was successful (step 1314). A 'no' determination to step 1314 results in the extract, transform, and load tool determining whether to retry the extract, transform, and loading cycle (step 1316). The load cycle might not be retried due to scheduling issues or because of certain types of errors that need to be addressed by a user or an information technology specialist. If the extract, transform, and load cycle is to be retried (a 'yes' determination to step 1316), the process returns to step 1310 and repeats. However, a 'no' determination to step 1316 results in extract, transform, and load tool generating an error message (step 1318). The error message can describe those errors that occurred during the extract, transform, and load cycle. This error message is sent back to the semantic conceptual mapping tool for analysis to identify the source of the error. The semantic conceptual mapping tool can, in some cases, automatically remedy the source of the error and then generate a new corrected semantic conceptual mapping. In other cases, the semantic conceptual mapping tool can assist the subject matter expert in resolving the source of the error manually. Thereafter, in this case, the semantic conceptual tool will generate a new corrected semantic conceptual mapping.

The extract, transform, and load tool then decides whether a new semantic conceptual mapping has been received (step 1320). A "yes" response to step 1320 results in the new semantic conceptual mapping being stored (step 1322). The process then returns to step 1300, turning control back over to the semantic conceptual mapping tool. A "no" response to step 1320 results in the process terminating.

Returning to step 1314, if the extract, transform, and load cycle was successful (a 'yes' determination to step 1314), then a determination is made whether one or more mapping errors exist after a successful loading (step 1324). This determination can be made by the extract, transform, and load tool, the semantic conceptual mapping tool, or by a human user. If the review shows any mapping errors, then all records with erroneous mappings should be removed from the conformed data target, such as conformed data target 512 of FIG. 5. Unmapping may be required if new knowledge comes to light after the semantic conceptual mapping has been executed utilizing an incorrect semantic conceptual mapping. The unloading of erroneous records can be performed immediately or scheduled for an unloading.

Thus, a determination, by a human or by the extract, transform, and load tool, is made whether to schedule unloading (step 1326). If unloading is to be performed (a 'yes' determination to step 1326), then the extract, transform, and load tool schedules the unloading cycle (step 1328). However, a 'no' determination to step 1326 results in the extract, transform, and load tool determining whether to perform additional loading (step 1330). If additional loading is to be performed (a 'yes' determination to step 1330), then the process returns to step 1310 and repeats. If additional loading is not to be performed (a 'no' determination to step 1330), then the process terminates.

Figure 14:
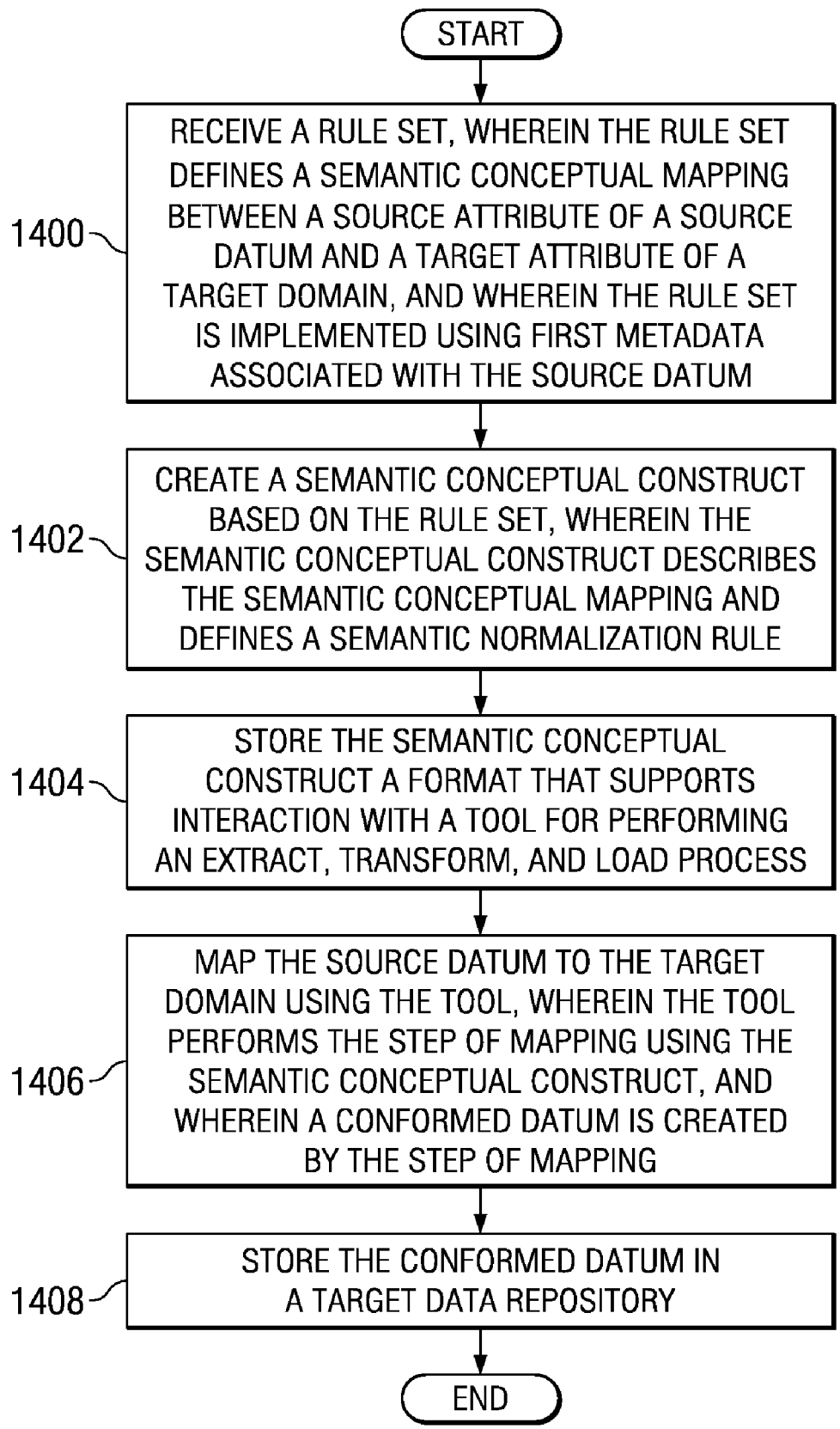
FIG. 14 is a flowchart illustrating performing an extract, transform, and load process using a metadata-based semantic conceptual mapping, in accordance with an illustrative embodiment.

FIG. 14 is a flowchart illustrating performing an extract, transform, and load process using metadata-based semantic conceptual mapping, in accordance with an illustrative embodiment. The process shown in FIG. 14 can be implemented in a data processing system, such as servers 104 and 106, or clients 110, 112, and 114 shown in FIG. 1, or data processing system 200 shown in FIG. 2. The process shown in FIG. 14 can be implemented using the combination of an extract, transform, and load tool, such as extract, transform, and load processor 522 shown in FIG. 5 or extract, transform, and load tool 614 in FIG. 6, and semantic conceptual mapping tool, such as semantic conceptual mapping tool 510 shown in FIG. 5, or semantic conceptual mapping tool 604 shown in FIG. 6. The process shown in FIG. 14 is an illustrative embodiment of the processes described with respect to FIG. 5 through FIGS. 13A and 13B.

The process begins as a semantic conceptual mapping tool receiving a rule set, wherein the rule set defines a semantic conceptual mapping between a source attribute of a source datum and a target attribute of a target domain, and wherein the rule set is implemented using first metadata associated with the source datum (step 1400). The semantic conceptual mapping tool creates a semantic conceptual construct based on the rule set, wherein the semantic conceptual construct describes the semantic conceptual mapping and defines a semantic normalization rule (step 1402). The semantic conceptual mapping tool stores the semantic conceptual construct in a format that supports interaction with a tool for performing an extract, transform, and load process (step 1404). The semantic conceptual mapping tool maps the source datum to the target domain using the tool, wherein the tool performs the step of mapping using the semantic conceptual construct, and wherein a conformed datum is created by the step of mapping (step 1406). Finally, the semantic conceptual mapping tool stores the conformed datum in a target data repository (step 1408).

FIG. 15 is a flowchart illustrating performing an extract, transform, and load process using metadata-based semantic conceptual mapping, in accordance with an illustrative embodiment. The process shown in FIG. 15 can be implemented in a data processing system, such as servers 104 and 106, or clients 110, 112, and 114 shown in FIG. 1, or data processing system 200 shown in FIG. 2. The process shown in FIG. 15 can be implemented using the combination of an extract, transform, and load tool, such as extract, transform, and load processor 522 shown in FIG. 5 or extract, transform, and load tool 614 in FIG. 6, and semantic conceptual mapping tool, such as semantic conceptual mapping tool 510 shown in FIG. 5, or semantic conceptual mapping tool 604 shown in FIG. 6. The process shown in FIG. 15 is an illustrative embodiment of the processes described with respect to FIG. 5 through FIG. 14.

The process begins as two or more target attributes are categorized into at least one domain, wherein the at least one domain has corresponding sets of domain (step 1500). Two or more source attributes are associated with the corresponding sets of domains, wherein associating creates a set of semantic conceptual definitions (step 1502). A target data structure is identified (step 1504). The target data structure is loaded (step 1506). Domain specifications associated with the sets of domains are themselves associated with the target data structure (step 1508). The set of semantic conceptual definitions can be stored in a semantic conceptual repository (step 1510). The process terminates thereafter.

FIG. 16 is a flowchart illustrating performing an extract, transform, and load process using metadata-based semantic conceptual mapping, in accordance with an illustrative embodiment. The process shown in FIG. 16 can be implemented in a data processing system, such as servers 104 and 106, or clients 110, 112, and 114 shown in FIG. 1, or data processing system 200 shown in FIG. 2. The process shown in FIG. 16 can be implemented using the combination of an extract, transform, and load tool, such as extract, transform, and load processor 522 shown in FIG. 5 or extract, transform, and load tool 614 in FIG. 6, and semantic conceptual mapping tool, such as semantic conceptual mapping tool 510 shown in FIG. 5, or semantic conceptual mapping tool 604 shown in FIG. 6. The process shown in FIG. 16 is an illustrative embodiment of the processes described with respect to FIG. 5 through FIG. 15.

The process begins as a semantic conceptual mapping tool is used to define a semantic conceptual mapping (step 1600). The semantic conceptual mapping is defined by a user. The semantic conceptual mapping maps a source datum to a target datum having a target attribute. The semantic conceptual mapping is defined using metadata. Source specific information is omitted from the semantic conceptual mapping. The semantic conceptual mapping tool then validates the semantic conceptual mapping by determining whether the semantic conceptual mapping is valid (step 1604). If the semantic conceptual mapping is not valid, then the process returns to step 1600 and repeats. However, if the semantic conceptual mapping is valid, then the semantic conceptual mapping is stored in a target data repository as a semantic conceptual construct. The process terminates thereafter.

Exemplary illustrative embodiments provide for a computer implemented method, apparatus, and computer usable program code for mapping data. A rule set is received. The rule set defines a semantic conceptual mapping between a source attribute of a source datum and a target attribute of a target domain. Furthermore, the rule set is implemented using first metadata associated with the source datum. A semantic conceptual construct is created based on the rule set. The semantic conceptual construct specifies the semantic conceptual mapping and is adapted to interact with a tool for performing an extract, transform, and load process. The source datum is mapped to the target domain using the tool. The tool performs the semantic conceptual mapping using the semantic conceptual construct. A conformed datum is created by the semantic conceptual mapping. The conformed datum is stored in a target data repository. In exemplary illustrative embodiments, the conformed datum and the source datum relate to healthcare claims records.

This exemplary embodiment can be used to create extract, transform, and load processes without referencing source attributes when constructing the mappings between source attributes and target domain attributes. Thus, users who have limited information technology knowledge can use the exemplary embodiments to define semantic conceptual mappings from an unclean source of data to a target data repository. Thereafter, existing tools can perform the actual extract, transform, and load process.

The illustrative embodiments are particularly useful in the healthcare research environment. The reason the illustrative embodiments are useful in this field, and other fields, is that subject matter experts who should define the semantic conceptual mappings can define the semantic conceptual mappings, which support an extract, transform, and load process—rather than relying on information technology experts with limited research knowledge to establish these semantic conceptual mappings.

Exemplary illustrative embodiments also provide for a computer implemented method, apparatus, and computer usable program code for mapping data. A semantic conceptual mapping is defined. The semantic conceptual mapping is defined by a user and maps a source datum to a target datum having a target attribute. The semantic conceptual mapping is defined using metadata and results in the generation of metadata which stores the semantic mapping rule set. The semantic conceptual mapping is stored in a semantic conceptual mapping data repository.

The invention can take the form of an entirely hardware embodiment, an entirely software embodiment or an embodiment containing both hardware and software elements. In a preferred embodiment, the invention is implemented in software, which includes, but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer-readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A data processing system comprising:
at least one processor;
a bus coupled to the at least one processor;
memory elements connected to the bus, wherein the memory elements contain a set of computer executable instructions for mapping data, wherein the at least one processor is adapted to carry out the set of computer executable instructions to:
receive a rule set, wherein the rule set defines a semantic conceptual mapping definition between a source attribute of a source datum and a target attribute of a target domain, wherein source specific information is omitted from the semantic conceptual mapping definition and wherein the rule set is implemented using first metadata associated with the source datum;

receive reference information from a reference source, wherein the reference source includes data dictionaries, online resources, custom vocabularies, lookup tables, code lists and semantic rules;

load a target definition;

populate the target definition organized according to the target domain, wherein the target definition is a data structure that defines how data is stored and a format of data in a conformed data target;

select the target domain for creation of a metadata based semantic conceptual mapping;

select a target domain attribute of the target domain;

determine a semantic conceptual mapping type;

select a source domain attribute;

deduce a data type of the source domain attribute;

create a semantic conceptual mapping from the source domain attribute to the target domain attribute using the reference information and the semantic conceptual mapping definition, wherein creating the semantic conceptual mapping further comprises validating the semantic conceptual mapping;

store the semantic conceptual mapping as a semantic conceptual construct wherein the semantic conceptual construct uses the semantic conceptual mapping type and the data type of the source domain attribute;

map the source domain attribute to the target domain attribute responsive to the semantic conceptual mapping being valid, using the semantic conceptual construct in accordance with the semantic conceptual mapping type and the data type of the source domain attribute, wherein a conformed datum is created and is integrated by capture of semantic equivalence via metadata; and store the conformed datum in a target data repository.

2. The data processing system of claim 1 wherein the semantic conceptual construct comprises data that defines a semantic conceptual mapping between the metadata associated with the source datum and second metadata associated with the target domain attribute.

3. The data processing system of claim 1 wherein the source datum comprises first clinical data related to a clinical study and the conformed datum comprises second clinical data related to the clinical study, wherein the first clinical data and the second clinical data convey the same information to a user, and wherein the first clinical data and the second clinical data are in different formats.

4. The data processing system of claim 3 wherein the source datum comprises first healthcare claims record data related to a healthcare claims record and the conformed datum comprises second clinical data related to the clinical study, wherein the first clinical data and the second clinical data convey a same information to a user, and wherein the first clinical data and the second clinical data are in different formats.

5. The data processing system of claim 1 wherein the rule set is created by a user who has limited information technology knowledge.

6. The data processing system of claim 1 wherein the at least one processor is further adapted to carry out the set of instructions to:

prevent the semantic conceptual mapping until the semantic conceptual construct is created.

7. The data processing system of claim 1 wherein the source datum comprises one of a name, a healthcare code, a language, a numerical value, a unit of measurement, a format, a date, a drug name, an industry classification, and a clinical term.

8. The data processing system of claim 1 wherein the conformed datum is stored at an atomic level.

9. The data processing system of claim 8 wherein the conformed datum is semantically equivalent to the source datum.

10. The data processing system of claim 8 wherein the target data repository is a database and wherein all levels of granularity of the database are conformed based on dimensions of the database.

11. The data processing system of claim 10 wherein the at least one processor is adapted to carry out the set of instructions to:

create an aggregation during extraction, transformation, and loading even if the aggregation did not exist in the underlying data source.

12. A computer implemented method comprising:

receiving a rule set, wherein the rule set defines a semantic conceptual mapping definition between a source attribute of a source datum and a target attribute of a target domain, wherein source specific information is omitted from the semantic conceptual mapping definition and wherein the rule set is implemented using first metadata associated with the source datum;

receiving reference information from a reference source, wherein the reference source includes data dictionaries, online resources, custom vocabularies, lookup tables, code lists and semantic rules;

loading a target definition;

populating the target definition organized according to a target domain, wherein the target definition is a data structure that defines how data is stored and a format of data in a conformed data target;

selecting the target domain for creation of a metadata based semantic conceptual mapping;

selecting a target domain attribute of the target domain;

determining a semantic conceptual mapping type;

selecting a source domain attribute;

deducing a data type of the source domain attribute;

creating a semantic conceptual mapping from the source domain attribute to the target domain attribute using the reference information and the semantic conceptual mapping definition, wherein creating the semantic conceptual mapping further comprises validating the semantic conceptual mapping;

storing the semantic conceptual mapping as a semantic conceptual construct wherein the semantic conceptual construct uses the semantic conceptual mapping type and the data type of the source domain attribute;

mapping the source domain attribute to the target domain attribute responsive to the semantic conceptual mapping being valid, using the semantic conceptual construct in accordance with the semantic conceptual mapping type and the data type of the source domain attribute, wherein a conformed datum is created and is integrated by capture of semantic equivalence via metadata; and storing the conformed datum in a target data repository.

13. The computer implemented method of claim 12 wherein validating the semantic conceptual mapping further comprises:

validating attribute mapping in the semantic conceptual mapping.

14. The computer implemented method of claim 13 wherein the target datum is stored at an atomic level.

15. The computer implemented method of claim 14 wherein the target data repository is a database and wherein all levels of granularity of the database are conformed based on dimensions of the database.

16. A computer program product comprising:
memory elements having computer executable program code stored therein for mapping data, the computer executable program code including:
computer executable program code for receiving a semantic conceptual mapping definition, wherein the semantic conceptual mapping is defined by a user, wherein the semantic conceptual mapping maps a source datum to a target datum having a target attribute, wherein the semantic conceptual mapping is defined using metadata, and wherein source specific information is omitted from the semantic conceptual mapping definition and wherein a rule set is implemented using first metadata associated with a source datum;
computer executable program code for receiving reference information from a reference source;
computer executable program code for loading a target definition;
computer executable program code for populating the target definition organized according to a target domain, wherein the target definition is a data structure that defines how data is stored and a format of data in a conformed data target;
computer executable program code for selecting the target domain for creation of a metadata based semantic conceptual mapping;
computer executable program code for selecting a target domain attribute of the target domain;
computer executable program code for determining a semantic conceptual mapping type;
computer executable program code for selecting a source domain attribute;
computer executable program code for deducing a data type of the source domain attribute;
computer executable program code for creating a semantic conceptual mapping from the source domain attribute to the target domain attribute using the reference information and the semantic conceptual mapping definition, wherein creating the semantic conceptual mapping further comprises validating the semantic conceptual mapping;
computer executable program code for determining whether the semantic conceptual mapping is valid; and
computer executable program code responsive to a determination that the semantic conceptual mapping is valid for storing the semantic conceptual mapping in a data repository as a semantic conceptual construct, wherein the semantic conceptual construct is responsive to the semantic conceptual mapping type and the data type of the source domain attribute.

17. The computer program product of claim 16 wherein the target datum is stored at an atomic level, wherein the target data repository is a database, and wherein all levels of granularity of the database are conformed based on dimensions of the database.

* * * * *